United States Patent
Darois et al.

(10) Patent No.: US 9,439,643 B2
(45) Date of Patent: Sep. 13, 2016

(54) INSTRUMENTS FOR DELIVERING TRANSFASCIAL SUTURES, TRANSFASCIAL SUTURE ASSEMBLIES, AND METHODS OF TRANSFASCIAL SUTURING

(75) Inventors: Roger E. Darois, Foster, RI (US); Donald E. Ziniti, Cumberland, RI (US); Kevin J. Ranucci, Warwick, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 210 days.

(21) Appl. No.: 13/157,155

(22) Filed: Jun. 9, 2011

(65) Prior Publication Data

US 2011/0306989 A1 Dec. 15, 2011

Related U.S. Application Data

(60) Provisional application No. 61/352,928, filed on Jun. 9, 2010.

(51) Int. Cl.
*A61B 17/04* (2006.01)
*A61B 17/00* (2006.01)
(Continued)

(52) U.S. Cl.
CPC ....... *A61B 17/0401* (2013.01); *A61B 17/0057* (2013.01); *A61B 17/0469* (2013.01);
(Continued)

(58) Field of Classification Search
CPC .......... A61B 17/0057; A61B 17/0469; A61B 17/0482; A61B 2017/00637; A61B 2017/00659; A61B 2017/00663; A61B 2017/0417; A61B 2017/0419; A61B 2017/047; A61B 2017/0472; A61B 2017/06009; A61B 2017/06052; A61B 2017/06057
USPC ....... 606/139, 142, 144, 145, 147, 148, 151, 606/232
See application file for complete search history.

(56) References Cited

U.S. PATENT DOCUMENTS 4,235,238 A 11/1980 Ogiu et al.
4,669,473 A 6/1987 Richards et al.
(Continued)

FOREIGN PATENT DOCUMENTS

DE 197 07 851 A1 9/1998
EP 1 762 185 A1 3/2007
(Continued)

OTHER PUBLICATIONS

Invitation to Pay Additional Fees and Communication Relating to the Results of the Partial International Search, mailed Sep. 12, 2011, for PCT/US2011/039793 (5 pages).
(Continued)

*Primary Examiner* — Eric Rosen
*Assistant Examiner* — Todd J Scherbel
(74) *Attorney, Agent, or Firm* — Wolf, Greenfield & Sacks, P.C.

(57) ABSTRACT

An instrument for delivering a suture transfascially may include a handle, a shaft extending from the handle, and a pair of needles that are moveable to an extended position beyond the end of the shaft. One or more sutures are carried by the instrument and may be delivered transfascially. A transfascial suture assembly includes a suture having a first segment, a second segment, and an intermediate segment therebetween. A force distributing member is locatable at the intermediate segment. Suture retainers may be provided at the end of each suture segment, and may be moveable relative to the suture segment connected therewith. A method of delivering transfascial sutures includes inserting a twin-needle instrument loaded with one or more sutures into an abdominal cavity and deploying, from within the abdominal cavity, the suture carrying needles through a soft tissue repair patch and then through at least part of the abdominal wall.

79 Claims, 22 Drawing Sheets

(51) Int. Cl.
*A61F 2/00* (2006.01)
*A61B 17/06* (2006.01)
*A61B 17/29* (2006.01)

(52) U.S. Cl.
CPC ......... *A61B17/0482* (2013.01); *A61F 2/0063* (2013.01); *A61B 17/0487* (2013.01); *A61B 2017/00663* (2013.01); *A61B 2017/0404* (2013.01); *A61B 2017/0409* (2013.01); *A61B 2017/0414* (2013.01); *A61B 2017/0417* (2013.01); *A61B 2017/0464* (2013.01); *A61B 2017/0472* (2013.01); *A61B 2017/0477* (2013.01); *A61B 2017/0488* (2013.01); *A61B 2017/0496* (2013.01); *A61B 2017/06009* (2013.01); *A61B 2017/06052* (2013.01); *A61B 2017/2923* (2013.01)

(56) References Cited

U.S. PATENT DOCUMENTS

| | | | |
|---|---|---|---|
| 4,696,300 | A | 9/1987 | Anderson |
| 4,935,027 | A | 6/1990 | Yoon |
| 5,041,129 | A | 8/1991 | Hayhurst et al. |
| 5,085,661 | A | 2/1992 | Moss |
| RE34,021 | E | 8/1992 | Mueller et al. |
| 5,226,426 | A | 7/1993 | Yoon |
| 5,281,237 | A | 1/1994 | Gimpelson |
| 5,290,217 | A | 3/1994 | Campos |
| 5,290,297 | A * | 3/1994 | Phillips .................. 606/144 |
| 5,364,408 | A | 11/1994 | Gordon |
| 5,366,480 | A | 11/1994 | Corriveau et al. |
| 5,391,182 | A | 2/1995 | Chin |
| 5,403,329 | A | 4/1995 | Hinchcliffe |
| 5,417,699 | A | 5/1995 | Klein et al. |
| 5,458,609 | A | 10/1995 | Gordon et al. |
| 5,462,560 | A | 10/1995 | Stevens |
| 5,470,337 | A | 11/1995 | Moss |
| 5,500,000 | A | 3/1996 | Feagin et al. |
| 5,501,692 | A | 3/1996 | Riza |
| 5,507,754 | A | 4/1996 | Green et al. |
| 5,507,755 | A | 4/1996 | Gresl et al. |
| 5,522,846 | A | 6/1996 | Bonutti |
| 5,527,343 | A | 6/1996 | Bonutti |
| 5,540,704 | A | 7/1996 | Gordon et al. |
| 5,549,631 | A | 8/1996 | Bonutti |
| 5,569,305 | A | 10/1996 | Bonutti |
| 5,575,800 | A | 11/1996 | Gordon |
| 5,578,044 | A | 11/1996 | Gordon et al. |
| 5,593,422 | A | 1/1997 | Muijs Van de Moer et al. |
| 5,611,515 | A | 3/1997 | Benderev et al. |
| 5,613,974 | A | 3/1997 | Andreas et al. |
| 5,618,290 | A | 4/1997 | Toy et al. |
| 5,620,012 | A | 4/1997 | Benderev et al. |
| 5,620,461 | A | 4/1997 | Muijs Van De Moer et al. |
| 5,626,614 | A | 5/1997 | Hart |
| 5,643,319 | A | 7/1997 | Green et al. |
| 5,662,664 | A | 9/1997 | Gordon et al. |
| 5,700,272 | A | 12/1997 | Gordon et al. |
| 5,713,910 | A * | 2/1998 | Gordon et al. ............... 606/144 |
| 5,722,981 | A | 3/1998 | Stevens |
| 5,733,306 | A | 3/1998 | Bonutti |
| 5,741,277 | A | 4/1998 | Gordon et al. |
| 5,741,279 | A | 4/1998 | Gordon et al. |
| 5,772,672 | A | 6/1998 | Toy et al. |
| 5,779,719 | A | 7/1998 | Klein et al. |
| 5,810,848 | A | 9/1998 | Hayhurst |
| 5,814,072 | A | 9/1998 | Bonutti |
| 5,836,315 | A | 11/1998 | Benderev et al. |
| 5,845,645 | A | 12/1998 | Bonutti |
| 5,868,762 | A | 2/1999 | Cragg et al. |
| 5,938,686 | A | 8/1999 | Benderev et al. |
| 5,941,439 | A | 8/1999 | Kammerer et al. |
| 5,944,739 | A | 8/1999 | Zlock et al. |
| 5,948,002 | A | 9/1999 | Bonutti |
| 5,954,747 | A | 9/1999 | Clark |
| 5,964,773 | A | 10/1999 | Greenstein |
| 6,022,360 | A | 2/2000 | Reimels et al. |
| 6,036,699 | A | 3/2000 | Andreas et al. |
| 6,048,351 | A | 4/2000 | Gordon et al. |
| 6,056,688 | A | 5/2000 | Benderev et al. |
| 6,056,773 | A | 5/2000 | Bonutti |
| 6,117,160 | A | 9/2000 | Bonutti |
| 6,159,234 | A | 12/2000 | Bonutti et al. |
| 6,206,895 | B1 | 3/2001 | Levinson |
| 6,210,416 | B1 | 4/2001 | Chu et al. |
| 6,245,080 | B1 | 6/2001 | Levinson |
| 6,280,460 | B1 | 8/2001 | Bolduc et al. |
| 6,287,317 | B1 | 9/2001 | Makower et al. |
| 6,293,952 | B1 | 9/2001 | Brosens et al. |
| 6,306,159 | B1 | 10/2001 | Schwartz et al. |
| 6,319,263 | B1 | 11/2001 | Levinson |
| 6,346,111 | B1 | 2/2002 | Gordon et al. |
| 6,355,050 | B1 | 3/2002 | Andreas et al. |
| 6,398,796 | B2 | 6/2002 | Levinson |
| 6,428,562 | B2 | 8/2002 | Bonutti |
| 6,500,184 | B1 | 12/2002 | Chan et al. |
| 6,500,195 | B2 | 12/2002 | Bonutti |
| 6,506,197 | B1 * | 1/2003 | Rollero et al. ................ 606/148 |
| 6,551,333 | B2 | 4/2003 | Kuhns et al. |
| 6,554,852 | B1 | 4/2003 | Oberlander |
| 6,565,590 | B2 * | 5/2003 | Kieturakis et al. ........... 606/190 |
| 6,592,609 | B1 | 7/2003 | Bonutti |
| 6,595,911 | B2 | 7/2003 | LoVuolo |
| 6,596,014 | B2 | 7/2003 | Levinson et al. |
| 6,626,930 | B1 | 9/2003 | Allen et al. |
| 6,635,073 | B2 | 10/2003 | Bonutti |
| 6,638,286 | B1 | 10/2003 | Burbank et al. |
| 6,692,506 | B1 | 2/2004 | Ory et al. |
| 6,699,263 | B2 | 3/2004 | Cope |
| 6,730,112 | B2 | 5/2004 | Levinson |
| 6,779,701 | B2 | 8/2004 | Bailly et al. |
| 6,821,285 | B2 | 11/2004 | Laufer et al. |
| 6,896,685 | B1 | 5/2005 | Davenport |
| 6,911,034 | B2 | 6/2005 | Nobles et al. |
| 6,939,357 | B2 | 9/2005 | Navarro et al. |
| 6,966,916 | B2 | 11/2005 | Kumar |
| 6,997,932 | B2 | 2/2006 | Dreyfuss et al. |
| 7,021,316 | B2 | 4/2006 | Leiboff |
| 7,033,370 | B2 | 4/2006 | Gordon et al. |
| 7,060,077 | B2 | 6/2006 | Gordon et al. |
| 7,087,073 | B2 | 8/2006 | Bonutti |
| 7,150,750 | B2 | 12/2006 | Damarati |
| 7,153,312 | B1 | 12/2006 | Torrie |
| 7,320,701 | B2 | 1/2008 | Haut et al. |
| 7,326,221 | B2 | 2/2008 | Sakamoto et al. |
| 7,381,210 | B2 | 6/2008 | Zarbatany et al. |
| 7,442,198 | B2 | 10/2008 | Gellman et al. |
| 7,445,626 | B2 | 11/2008 | Songer et al. |
| 7,569,063 | B2 | 8/2009 | Bailly et al. |
| 7,572,267 | B2 | 8/2009 | Manzo |
| 7,608,092 | B1 | 10/2009 | Schaffhausen |
| 7,618,449 | B2 | 11/2009 | Tremulis et al. |
| 7,645,286 | B2 | 1/2010 | Catanese, III et al. |
| 7,722,629 | B2 | 5/2010 | Chambers |
| 7,722,633 | B2 | 5/2010 | Laufer et al. |
| 7,740,638 | B2 | 6/2010 | Hyde |
| 7,771,438 | B2 | 8/2010 | Dreyfuss et al. |
| 7,780,682 | B2 | 8/2010 | Catanese, III et al. |
| 7,815,659 | B2 | 10/2010 | Conlon et al. |
| 7,815,662 | B2 | 10/2010 | Spivey et al. |
| 7,846,179 | B2 | 12/2010 | Belef et al. |
| 7,850,712 | B2 | 12/2010 | Conlon et al. |
| 7,879,048 | B2 | 2/2011 | Bain |
| 7,918,868 | B2 | 4/2011 | Marshall et al. |
| 7,942,886 | B2 | 5/2011 | Alvarado |
| 7,959,640 | B2 | 6/2011 | Kantsevoy et al. |
| 8,105,342 | B2 | 1/2012 | Onuki et al. |
| 8,512,375 | B2 | 8/2013 | Torrie et al. |
| 8,702,753 | B2 | 4/2014 | Mikkaichi et al. |
| 8,790,356 | B2 | 7/2014 | Darois et al. |
| 2001/0021856 | A1 | 9/2001 | Bolduc et al. |
| 2002/0019649 | A1 | 2/2002 | Sikora et al. |
| 2002/0103494 | A1 | 8/2002 | Pacey |

(56) References Cited

U.S. PATENT DOCUMENTS

| | | |
|---|---|---|
| 2003/0045891 A1 | 3/2003 | Yamamoto et al. |
| 2003/0105489 A1 | 6/2003 | Eichhorn et al. |
| 2003/0236535 A1 | 12/2003 | Onuki |
| 2004/0044364 A1 | 3/2004 | DeVries et al. |
| 2004/0092969 A1* | 5/2004 | Kumar .................. 606/151 |
| 2004/0133238 A1 | 7/2004 | Cerier |
| 2004/0138683 A1 | 7/2004 | Shelton et al. |
| 2004/0260343 A1 | 12/2004 | Leclair |
| 2005/0033363 A1 | 2/2005 | Bojarski et al. |
| 2005/0043746 A1 | 2/2005 | Pollak et al. |
| 2005/0049635 A1* | 3/2005 | Leiboff .................. 606/213 |
| 2005/0075654 A1 | 4/2005 | Kelleher |
| 2005/0228407 A1 | 10/2005 | Nobles et al. |
| 2005/0288689 A1 | 12/2005 | Kammerer et al. |
| 2006/0020247 A1 | 1/2006 | Kagan et al. |
| 2006/0025819 A1 | 2/2006 | Nobis et al. |
| 2006/0030868 A1 | 2/2006 | Bennett |
| 2006/0069399 A1 | 3/2006 | Weisel et al. |
| 2006/0116718 A1 | 6/2006 | Leiboff |
| 2006/0142784 A1 | 6/2006 | Kontos |
| 2006/0178680 A1 | 8/2006 | Nelson et al. |
| 2006/0235446 A1 | 10/2006 | Godin |
| 2006/0265009 A1 | 11/2006 | Bonutti |
| 2006/0265011 A1 | 11/2006 | Bonutti |
| 2006/0265042 A1 | 11/2006 | Catanese et al. |
| 2006/0271101 A1 | 11/2006 | Saadat et al. |
| 2006/0276871 A1 | 12/2006 | Lamson et al. |
| 2006/0293709 A1 | 12/2006 | Bojarski et al. |
| 2007/0027476 A1 | 2/2007 | Harris et al. |
| 2007/0049970 A1* | 3/2007 | Belef et al. .................. 606/232 |
| 2007/0073319 A1 | 3/2007 | Mikkaichi et al. |
| 2007/0118153 A1 | 5/2007 | Funamura et al. |
| 2007/0149987 A1 | 6/2007 | Wellman et al. |
| 2007/0185532 A1 | 8/2007 | Stone et al. |
| 2007/0191886 A1 | 8/2007 | Dejima et al. |
| 2007/0203507 A1 | 8/2007 | McLaughlin et al. |
| 2007/0213757 A1 | 9/2007 | Boraiah |
| 2007/0276408 A1 | 11/2007 | Filipi et al. |
| 2007/0276414 A1 | 11/2007 | Nobles |
| 2007/0293876 A1 | 12/2007 | Abe et al. |
| 2008/0021484 A1 | 1/2008 | Catanese et al. |
| 2008/0039889 A1 | 2/2008 | Lamson et al. |
| 2008/0065120 A1 | 3/2008 | Zannis et al. |
| 2008/0086154 A1 | 4/2008 | Taylor et al. |
| 2008/0114378 A1 | 5/2008 | Matsushita |
| 2008/0114399 A1 | 5/2008 | Bonutti |
| 2008/0140092 A1 | 6/2008 | Stone et al. |
| 2008/0154286 A1 | 6/2008 | Abbott et al. |
| 2008/0161850 A1 | 7/2008 | Weisenburgh et al. |
| 2008/0177288 A1* | 7/2008 | Carlson .............. A61B 17/0057 606/144 |
| 2008/0208220 A1 | 8/2008 | Shiono et al. |
| 2008/0228265 A1 | 9/2008 | Spence et al. |
| 2008/0228266 A1 | 9/2008 | McNamara et al. |
| 2008/0243148 A1 | 10/2008 | Mikkaichi et al. |
| 2008/0255591 A1 | 10/2008 | Harada et al. |
| 2008/0294001 A1 | 11/2008 | Surti |
| 2009/0023997 A1 | 1/2009 | Stokes et al. |
| 2009/0062743 A1 | 3/2009 | Rotella et al. |
| 2009/0062817 A1 | 3/2009 | Suzuki et al. |
| 2009/0069823 A1 | 3/2009 | Foerster et al. |
| 2009/0082786 A1 | 3/2009 | Surti |
| 2009/0082806 A1 | 3/2009 | West, Jr. et al. |
| 2009/0088780 A1 | 4/2009 | Shiono et al. |
| 2009/0112232 A1 | 4/2009 | Crainich et al. |
| 2009/0112234 A1 | 4/2009 | Crainich et al. |
| 2009/0118734 A1 | 5/2009 | Bhatnagar et al. |
| 2009/0118762 A1 | 5/2009 | Crainch et al. |
| 2009/0125039 A1 | 5/2009 | Mikkaichi et al. |
| 2009/0156997 A1 | 6/2009 | Trenhaile |
| 2009/0163939 A1 | 6/2009 | Mabuchi et al. |
| 2009/0171140 A1 | 7/2009 | Chu |
| 2009/0192439 A1 | 7/2009 | Lamson et al. |
| 2009/0204147 A1 | 8/2009 | Rahmani |
| 2009/0216253 A1 | 8/2009 | Bell et al. |
| 2009/0216265 A1 | 8/2009 | DeVries et al. |
| 2009/0228041 A1 | 9/2009 | Domingo |
| 2009/0275961 A1 | 11/2009 | Harris et al. |
| 2009/0281568 A1 | 11/2009 | Cendan |
| 2009/0292302 A1 | 11/2009 | Manzo |
| 2009/0312603 A1 | 12/2009 | Lam et al. |
| 2009/0326566 A1* | 12/2009 | Alvarado .................. 606/153 |
| 2010/0010448 A1 | 1/2010 | Deckard |
| 2010/0016870 A1 | 1/2010 | Campbell |
| 2010/0023025 A1 | 1/2010 | Zeiner et al. |
| 2010/0023026 A1 | 1/2010 | Zeiner et al. |
| 2010/0030236 A1 | 2/2010 | Hayashi et al. |
| 2010/0036395 A1 | 2/2010 | Miller |
| 2010/0042114 A1 | 2/2010 | Schaffhausen |
| 2010/0069930 A1* | 3/2010 | Roslin et al. .................. 606/151 |
| 2010/0076462 A1 | 3/2010 | Bakos et al. |
| 2010/0076488 A1 | 3/2010 | Spivey et al. |
| 2010/0106166 A1 | 4/2010 | Cropper et al. |
| 2010/0121353 A1 | 5/2010 | Marshall et al. |
| 2010/0145364 A1 | 6/2010 | Keren et al. |
| 2010/0174299 A1 | 7/2010 | Viola et al. |
| 2010/0234854 A1 | 9/2010 | Abbott et al. |
| 2010/0249809 A1 | 9/2010 | Singhatat et al. |
| 2010/0262166 A1 | 10/2010 | Boraiah et al. |
| 2010/0292712 A1 | 11/2010 | Nering et al. |
| 2010/0292719 A1 | 11/2010 | Ducharme |
| 2010/0324573 A1 | 12/2010 | Toubia et al. |
| 2011/0082472 A1 | 4/2011 | Harris et al. |
| 2011/0112434 A1 | 5/2011 | Ghabrial et al. |
| 2011/0125189 A1 | 5/2011 | Stoll, Jr. et al. |
| 2011/0166598 A1 | 7/2011 | Gonazles et al. |
| 2012/0035626 A1 | 2/2012 | Chu |
| 2012/0143220 A1 | 6/2012 | Morgan et al. |
| 2012/0143221 A1 | 6/2012 | Weisel et al. |

FOREIGN PATENT DOCUMENTS

| | | |
|---|---|---|
| EP | 1 769 749 A1 | 4/2007 |
| EP | 1 808 134 A2 | 7/2007 |
| JP | 5-161655 | 6/1993 |
| JP | 2004-000601 A | 1/2004 |
| JP | 2008-093431 A | 4/2008 |
| WO | WO 98/46142 A1 | 10/1998 |
| WO | WO 99/45848 A1 | 9/1999 |
| WO | WO 02/053011 A2 | 7/2002 |
| WO | WO 2004/008973 A1 | 1/2004 |
| WO | WO 2004/098415 A2 | 11/2004 |
| WO | WO 2009/126781 A1 | 10/2009 |
| WO | WO 2011/039732 A1 | 4/2011 |
| WO | WO 2011/123714 A1 | 10/2011 |

OTHER PUBLICATIONS

Final Office Action for U.S. Appl. No. 13/157,182, mailed Jul. 5, 2013 (13 pages).

Final Office Action for U.S. Appl. No. 13/290,222 mailed Dec. 4, 2013 (16 pages).

Office Action for U.S. Appl. No. 13/157,172 mailed on Oct. 18, 2013 (9 pages).

Office Action for U.S. Appl. No. 13/416,740, mailed Oct. 25, 2013 (13 pages).

Office Action for U.S. Appl. No. 13/157,182, mailed on Oct. 10, 2012 (12 pages).

Office Action for U.S. Appl. No. 13/290,222, mailed on Apr. 2, 2013 (12 pages).

International Search Report and Written Opinion of the International Searching Authority for International Application No. PCT/US2011/039793, mailed Dec. 20, 2011 (22 pages).

Final Office Action for U.S. Appl. No. 13/157,172 mailed Apr. 3, 2014 (11 pages).

Office Action for U.S. Appl. No. 13/157,182, mailed Aug. 5, 2014 (12 pages).

Office Action for U.S. Appl. No. 13/290,247, mailed Oct. 3, 2014 (13 pages).

Office Action for U.S. Appl. No. 13/290,222, mailed on Oct. 31, 2014 (19 pages).

(56) References Cited

OTHER PUBLICATIONS

English translation of Notice of Reasons for Rejection for Japanese patent application 2013-514368, dated Jan. 28, 2015 (4 pages).
Office Action for U.S. Appl. No. 13/157,172 mailed on Feb. 12, 2015 (8 pages).
Final Office Action for U.S. Appl. No. 13/157,182, mailed Feb. 25, 2015 (14 pages).
Office Action for U.S. Appl. No. 13/290,236, mailed Dec. 14, 2015 (11 pages).
Office Action for U.S. Appl. No. 13/157,172, mailed Jan. 6, 2016 (12 pages).
Office Action for U.S. Appl. No. 13/157,182, mailed Aug. 19, 2015 (12 pages).
Final Office Action for U.S. Appl. No. 13/157,172, mailed Aug. 31, 2015 (12 pages).
Office Action for U.S. Appl. No. 14/353,938, dated Apr. 22, 2016 (14 pages).

\* cited by examiner

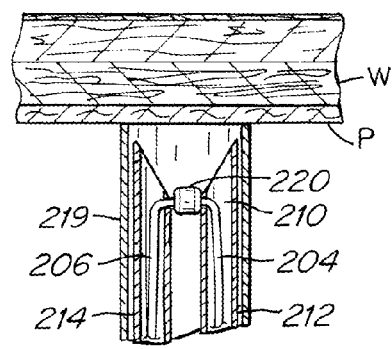
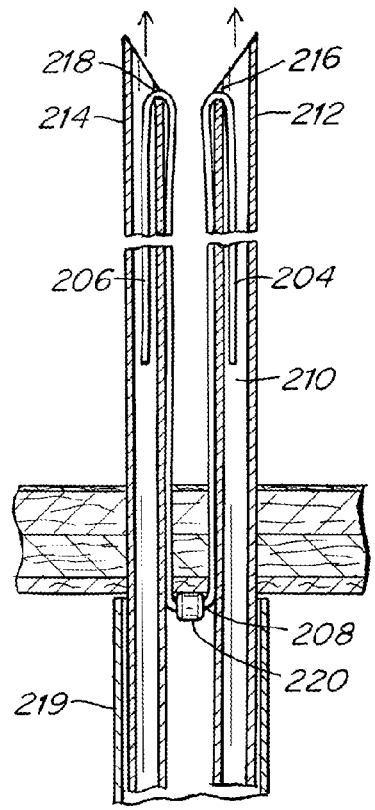
Fig. 5A
Fig. 5B
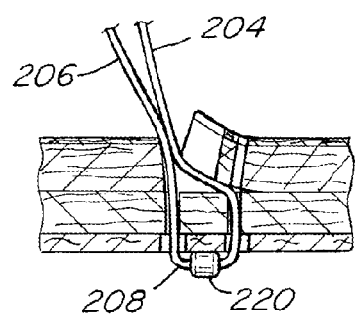
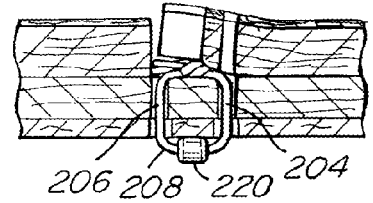
Fig. 5C
Fig. 5D

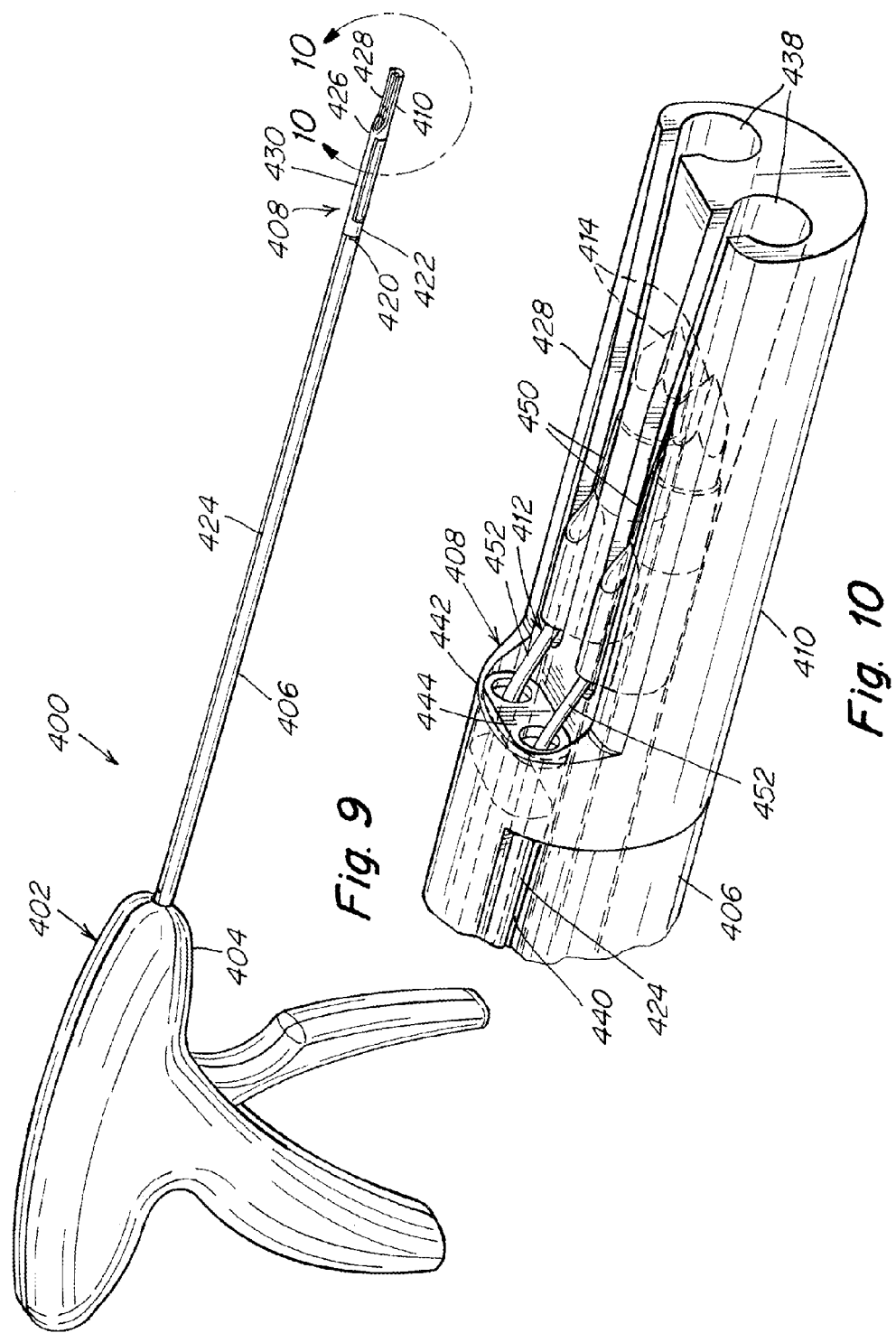

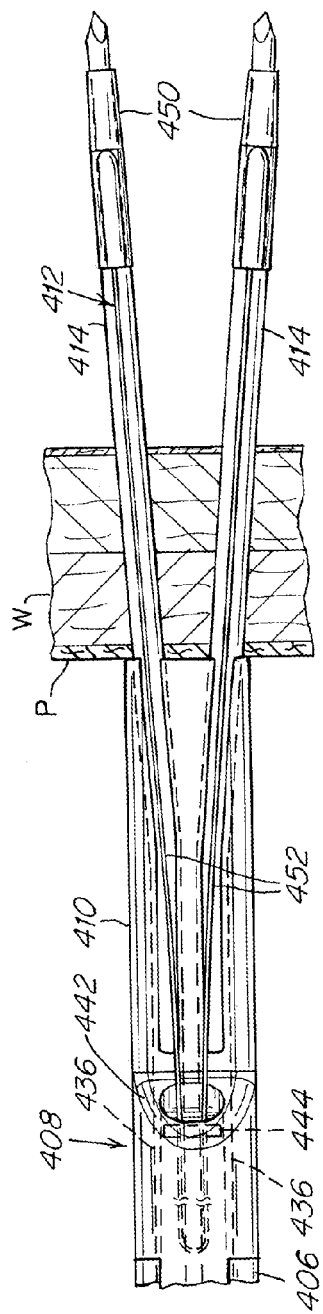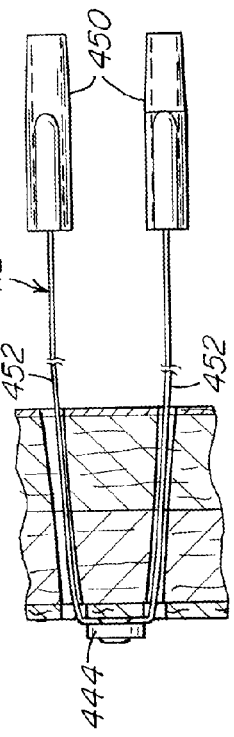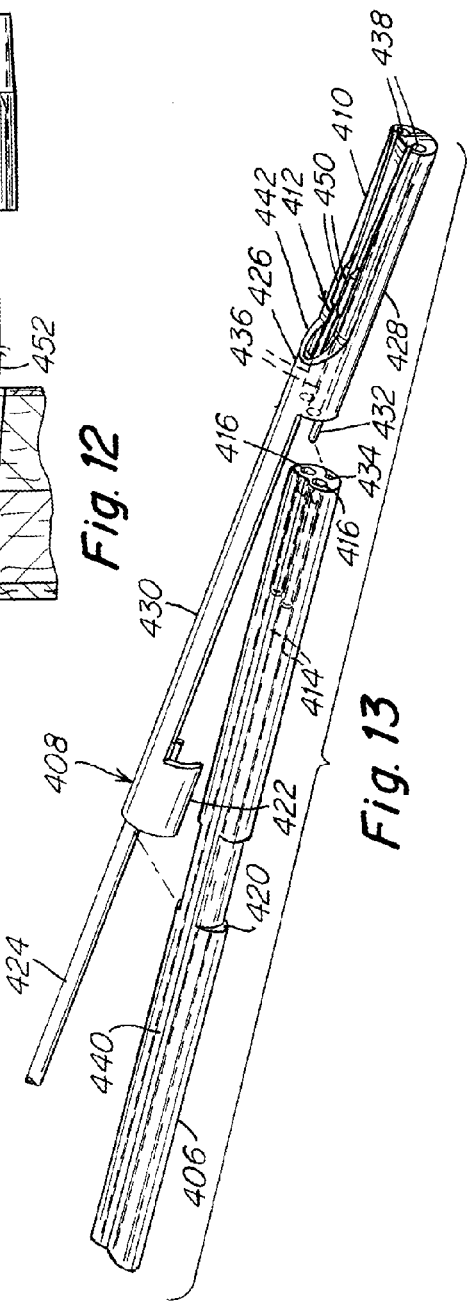

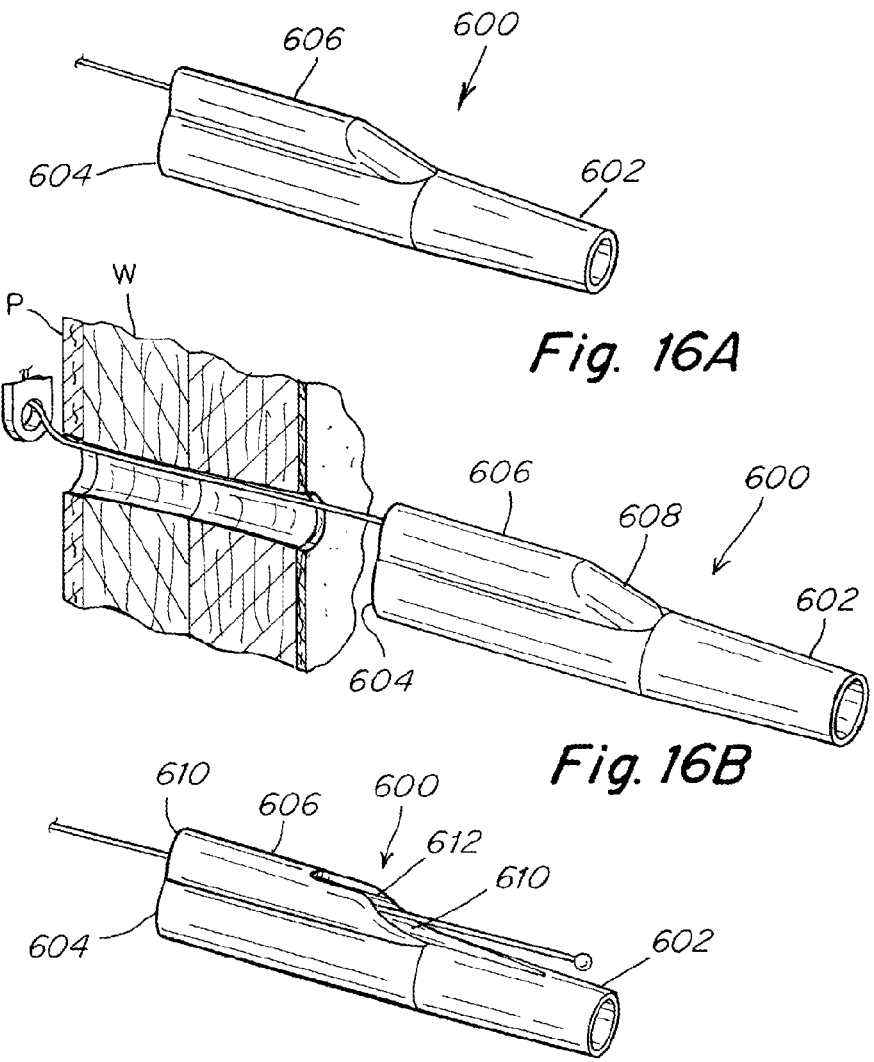
Fig. 16A
Fig. 16B
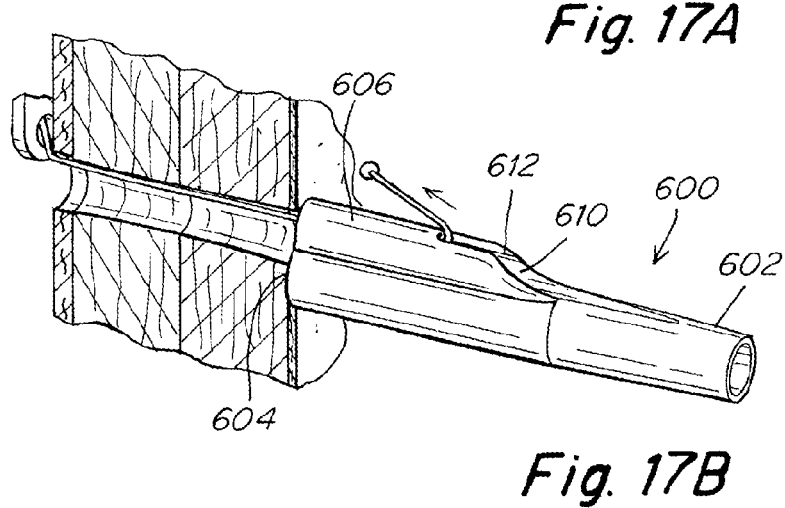
Fig. 17A
Fig. 17B

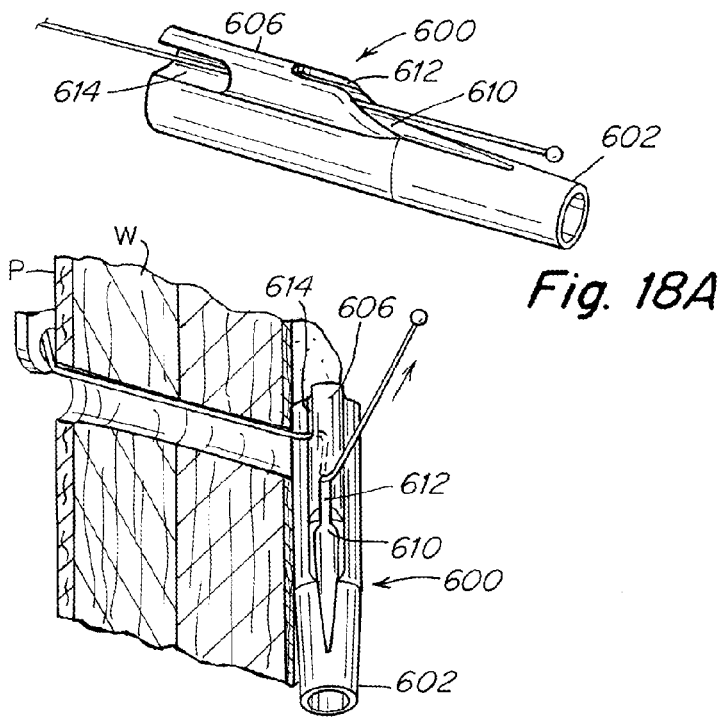
*Fig. 18A*
*Fig. 18B*
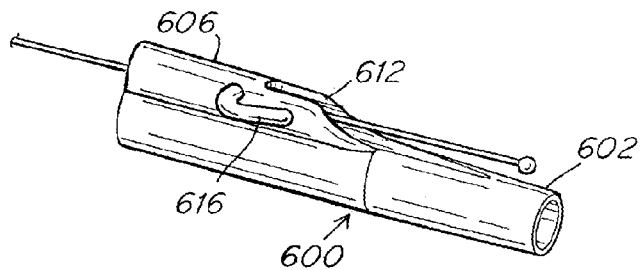
*Fig. 19A*
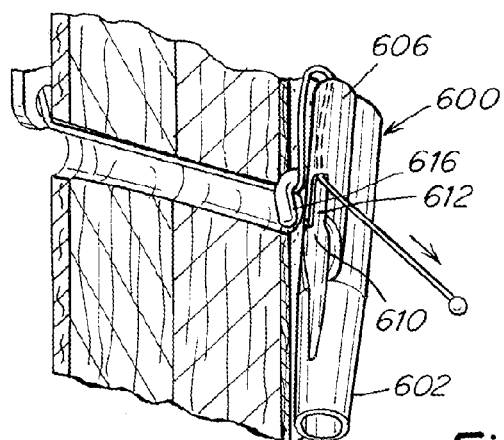
*Fig. 19B*

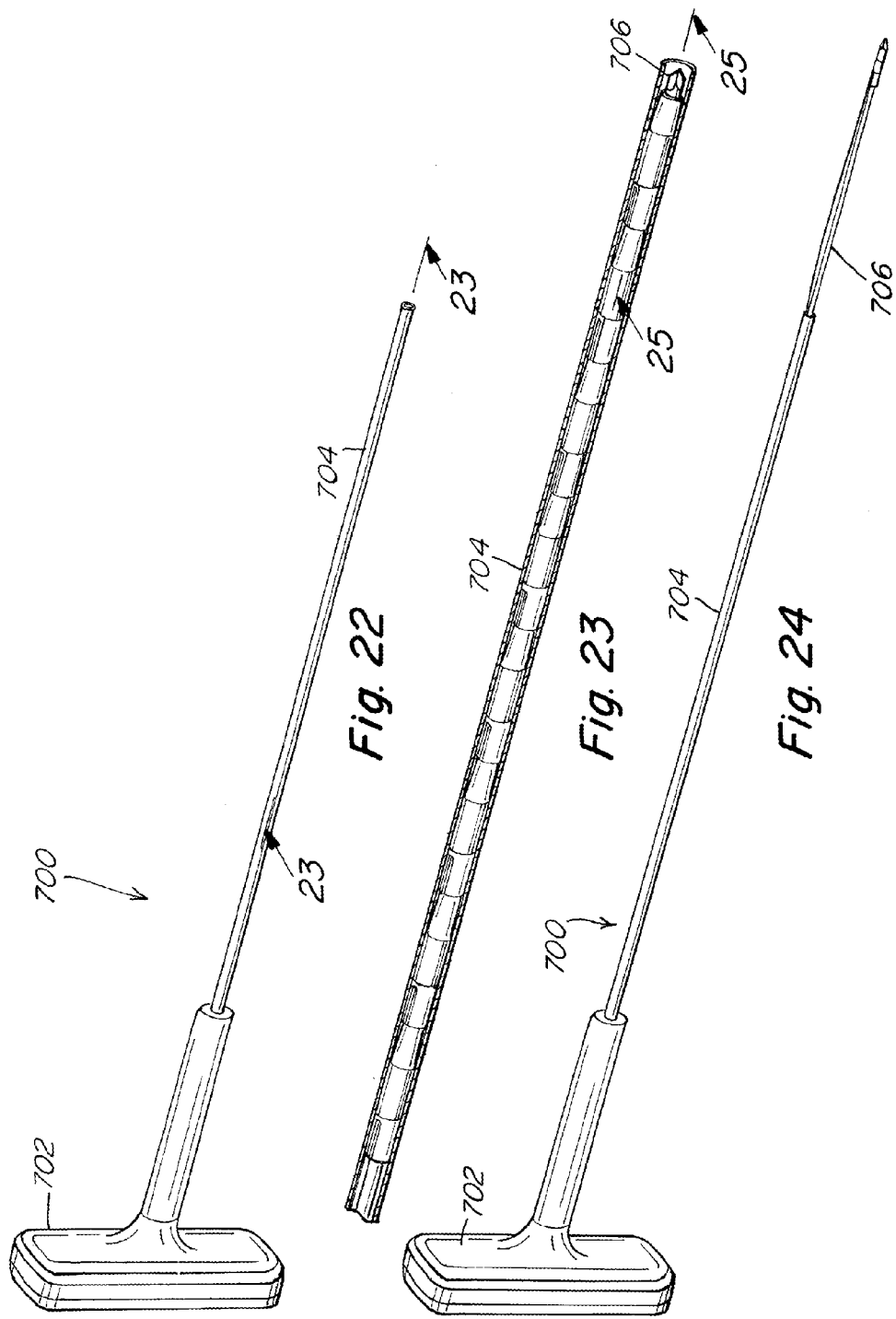

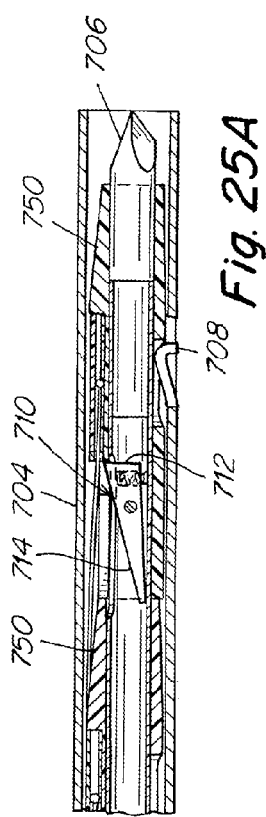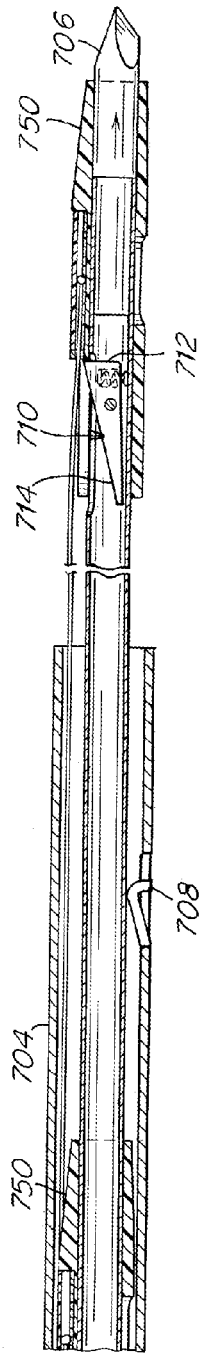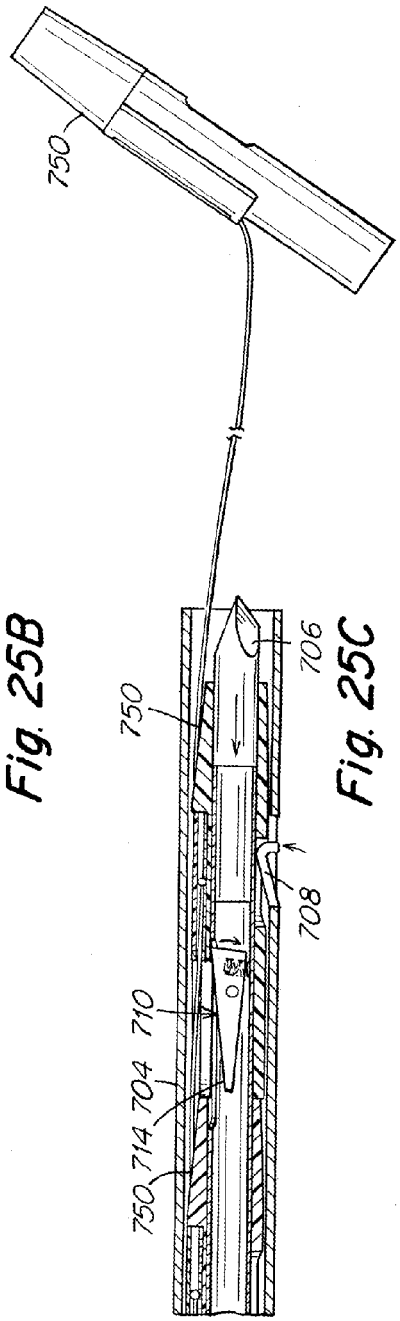

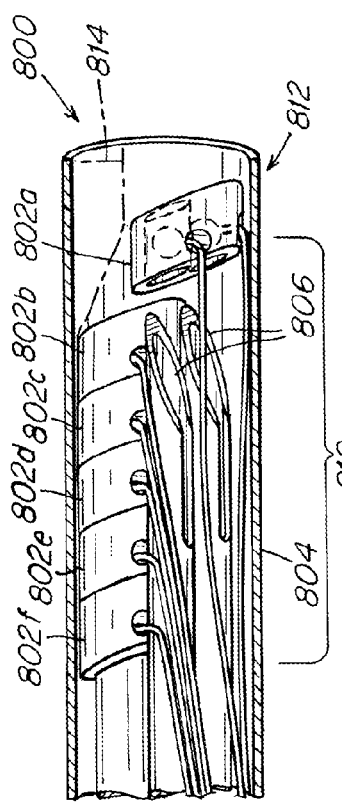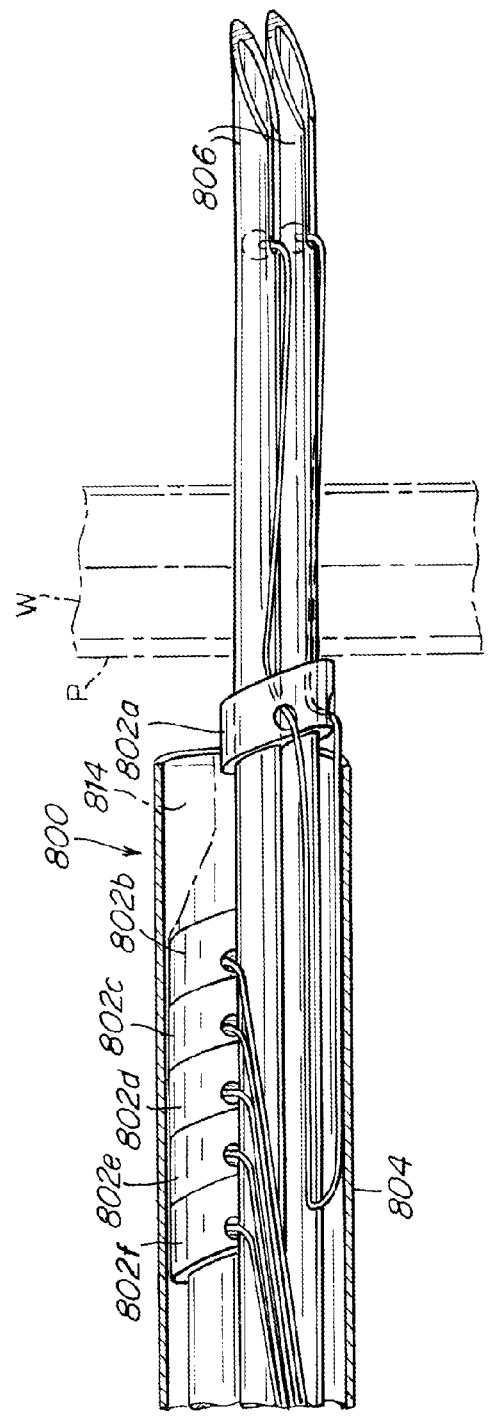

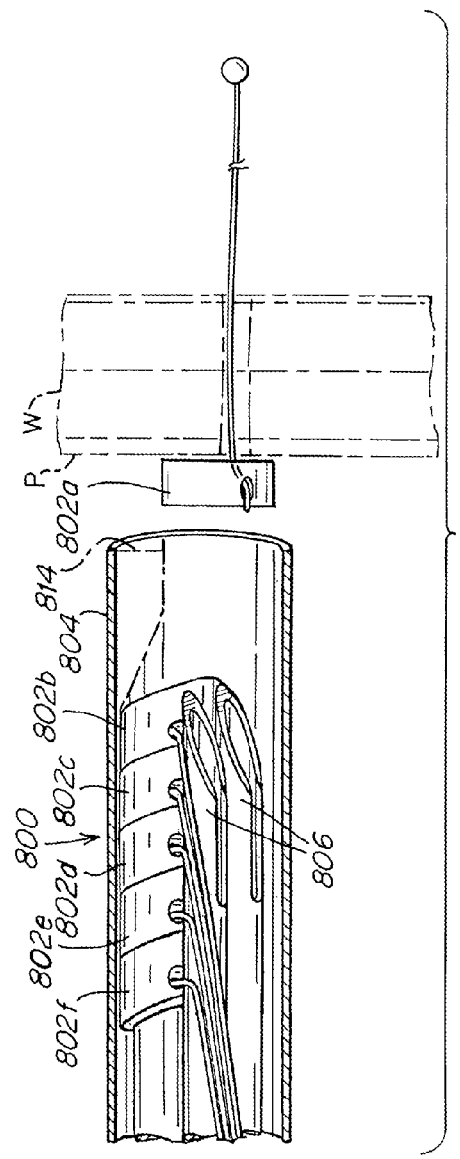
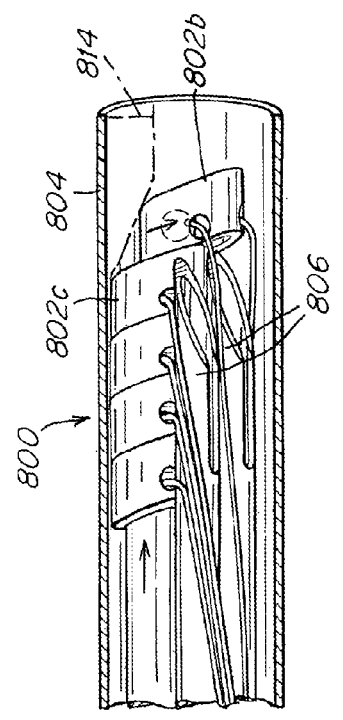
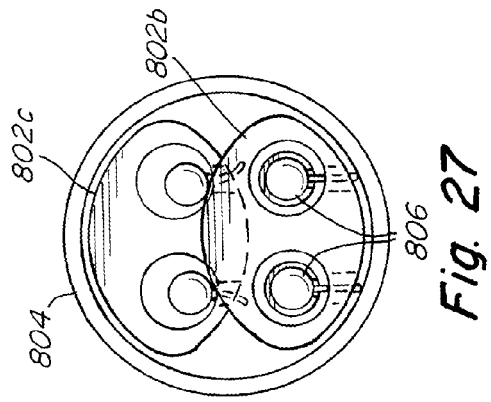
Fig. 26C
Fig. 26D
Fig. 27

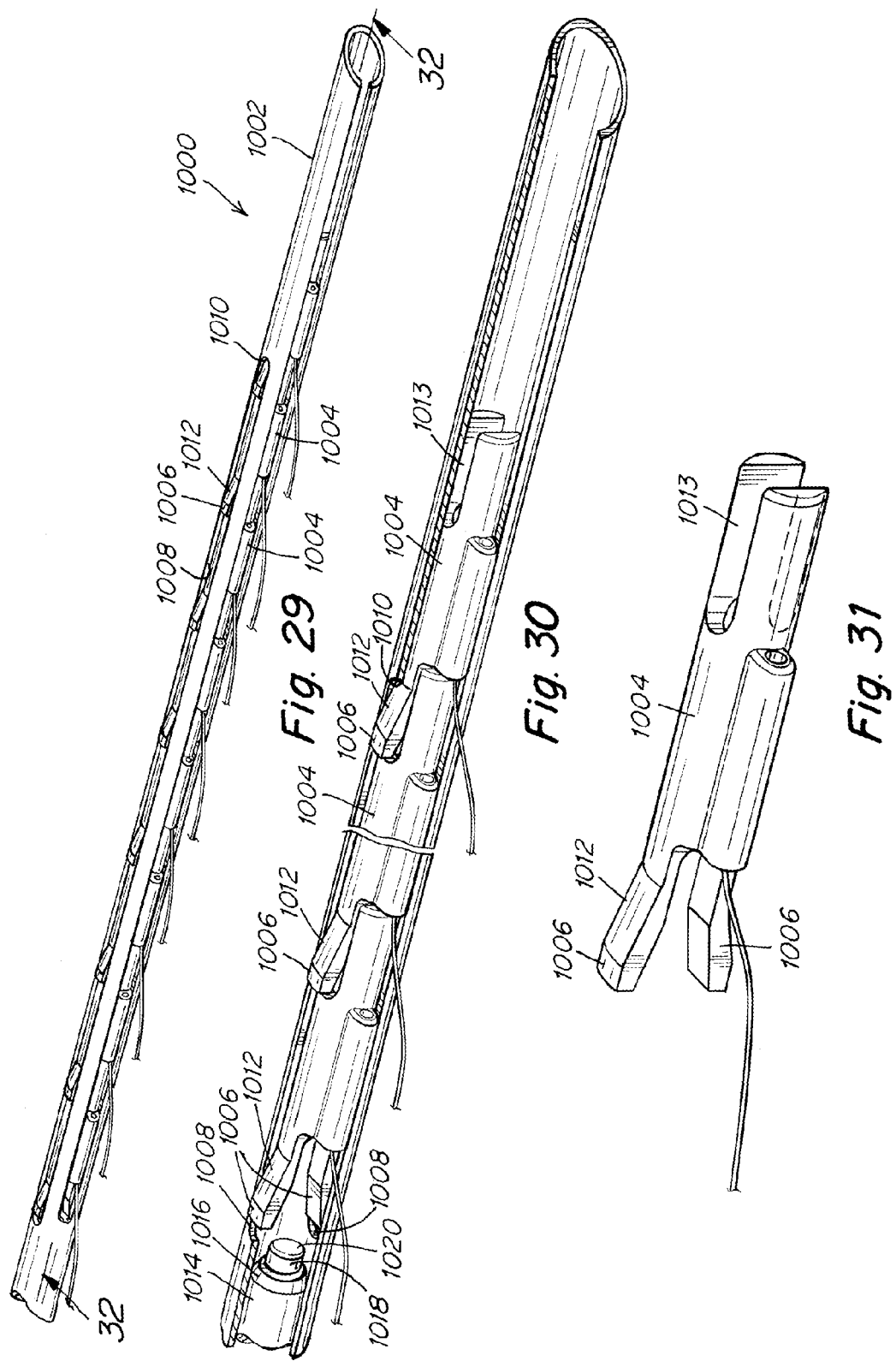

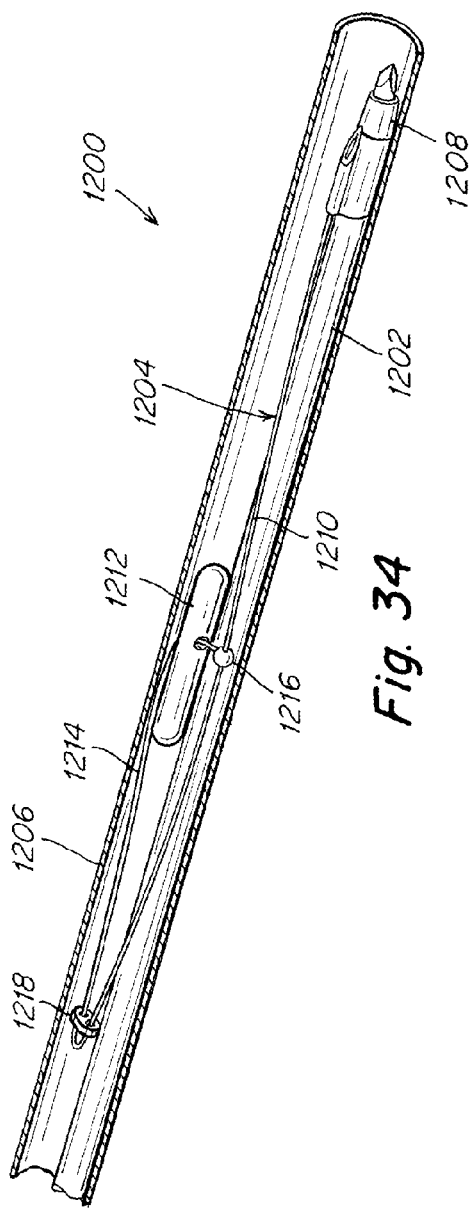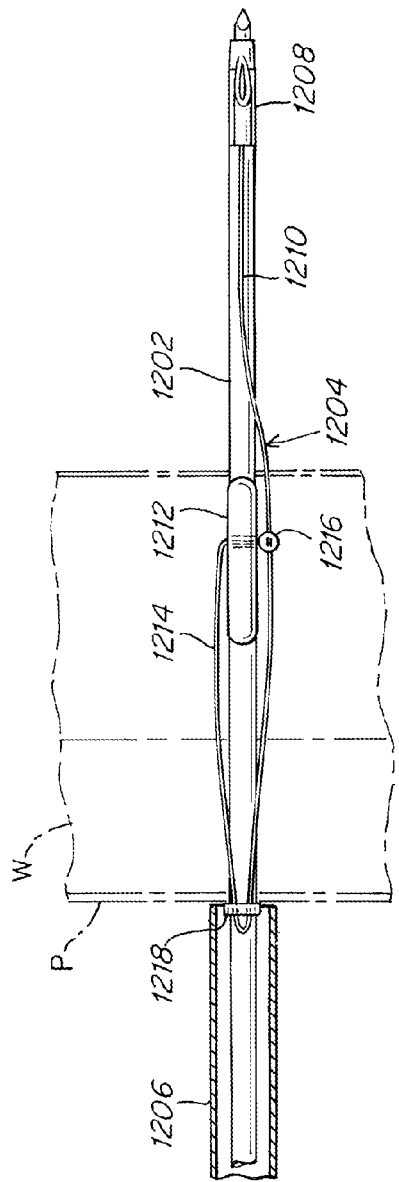
Fig. 34
Fig. 34A

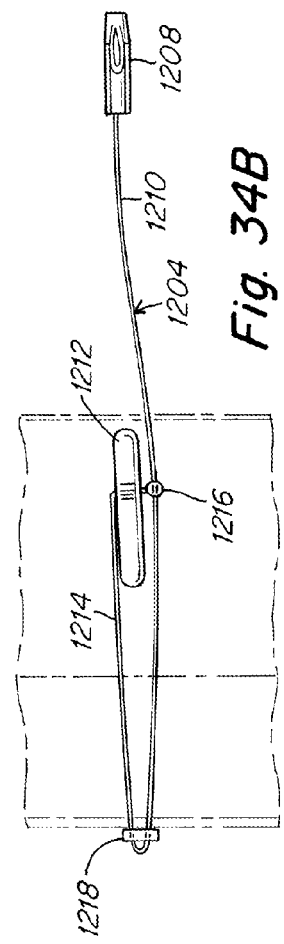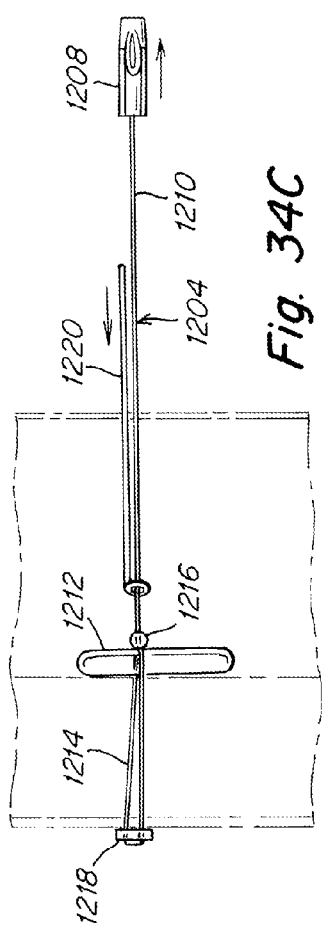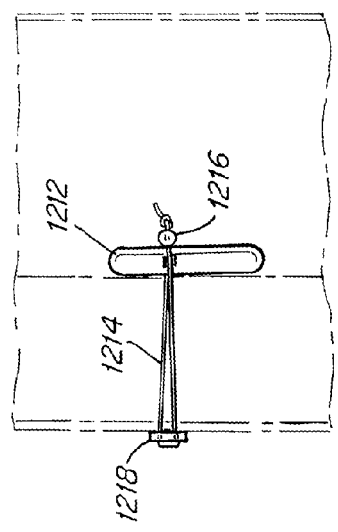

INSTRUMENTS FOR DELIVERING TRANSFASCIAL SUTURES, TRANSFASCIAL SUTURE ASSEMBLIES, AND METHODS OF TRANSFASCIAL SUTURING

FIELD

The invention relates to instruments for delivering transfascial sutures, to transfascial suture assemblies, and to methods of transfascial suturing.

BACKGROUND

Ventral hernia repair routinely involves placement of a soft tissue repair prosthetic, typically in the form of a patch, across an abdominal wall defect. In a laparoscopic procedure, or other minimally invasive approach, the patch is reduced in size and delivered through a narrow cannula or incision into the abdominal cavity where it then is returned to an expanded shape and deployed against the abdominal wall. Sutures may be applied through a partial, if not full, thickness of the abdominal wall (i.e., transfascial suturing). Additionally, or alternatively, tacks, screws, coils or other fasteners may be placed through the patch into just the innermost layers of the abdominal wall, such as the peritoneum and posterior fascia.

A conventional approach for transfascial suture delivery, as shown in FIG. 1, proceeds from outside of the patient. Sutures are pre-tied at spaced locations 100 about a patch 102 periphery, with pairs of suture tails 104 extending from each knot. It is these tails that will bridge the fascia and be secured together to form the transfascial suture fixation. The patch, pre-loaded with sutures, is collapsed and delivered into the abdominal cavity.

A suture passer instrument 106 is inserted, from outside of the patient, through the abdominal wall 108 and into the abdominal cavity in the approximate location of a particular suture tail pair. The suture passer includes a jaw or other grasper type arrangement which is operated within the cavity to capture one of the suture tails. The suture passer is retracted back through and out of the abdominal wall, drawing the suture tail exteriorly of the abdominal cavity. A hemostat or other clamp is applied to the exposed suture tail, preventing slippage of the suture tail back into the abdominal cavity. The suture passer is inserted again through the abdominal wall, creating a new puncture adjacent the first puncture, and operated to grab the remaining suture tail. The suture passer is pulled outwardly from the abdominal cavity, retrieving the second suture tail which also can be clamped against the anterior fascia. This standard transfascial suturing technique, approached from outside of the abdominal cavity, is repeated until all of the suture tail pairs have been transfascially deployed and tied together, typically at small skin incisions such that the tied knots are in the subcutaneous space.

SUMMARY

One aspect of the invention is a method of delivering a transfascial suture including providing a soft tissue repair prosthetic in an abdominal cavity of a patient and then passing, from within the abdominal cavity, a suture first through the soft tissue repair prosthetic and then through at least a part of the abdominal wall.

Another aspect of the invention is a method of delivering a transfascial suture with a suturing instrument that has been inserted into an abdominal cavity. The suturing instrument has a pair of needles and is loaded with at least one suture defined by a pair of suture segments, with each needle being associated with one of the pair of suture segments. Each of the needles is advanced from the suturing instrument through at least a part of the abdominal wall.

Another aspect of the invention is a method of delivering a transfascial suture including the acts of providing a suture that is defined by a pair of segments, each segment having a tail end and a section proximal the tail end, and passing each proximal section of a suture segment, before passing each tail end, through at least a portion of the abdominal wall.

Another aspect of the invention is a method of delivering a transfascial suture including providing a soft tissue repair prosthetic, and a suture defined by a pair of segments, each segment including a suture retainer, in an abdominal cavity. Passing, from within the abdominal cavity, each of the suture retainers through the soft tissue repair prosthetic and at least part of the abdominal wall, with each of the suture segments following a respective suture retainer through the soft tissue repair prosthetic and abdominal wall. The pair of suture segments that have passed through the abdominal wall are then secured together, such as by tying.

Another aspect of the invention is a method of delivering a transfascial suture including the acts of creating an opening in a soft tissue repair prosthetic located in an abdominal cavity by passing a suture through the soft tissue repair prosthetic, and then at least partially covering the opening with a force distributing member carried by the suture.

Another aspect of the invention is a method of inserting an instrument into an abdominal cavity. The instrument includes at least one tissue piercing member having a sharp end adapted to pierce abdominal wall tissue, and the instrument has a non-piercing mode with the sharp end of the tissue piercing member being shielded against contact with abdominal wall tissue and a piercing mode with the sharp end of the tissue piercing member being available for contact with abdominal wall tissue. The method includes inserting the instrument in the non-piercing mode into the abdominal cavity with the sharp end of the at least one tissue piercing member being shielded from contact with the abdominal wall tissue, and positioning the instrument in the non-piercing mode adjacent the abdominal wall. After positioning the instrument, the instrument is actuated to the piercing mode, and the at least one tissue piercing member is advanced through at least a part of the abdominal wall with the instrument in the piercing mode.

Another aspect of the invention is an instrument for delivering a transfascial suture including a handle and an elongated shaft extending from the handle, the shaft including a distal end. The instrument also includes a first needle and a second needle, the first and second needles being moveable to an extended position beyond the distal end of the shaft. Each needle has a sharp end adapted to pierce a soft tissue repair prosthetic and abdominal wall tissue. A suture is carried by the instrument, the suture defined by a first segment and a second segment, and including a suture force distributing member between the first and second segments. The suture is arranged in the instrument so that the suture segments are carried by the needles as the needles move to the extended position.

Another aspect of the invention is an instrument for delivering a transfascial suture including a handle and an elongated shaft extending from the handle, the shaft including a distal end. The instrument also includes a first needle and a second needle, the first and second needles being moveable to an extended position beyond the distal end of the shaft. Each needle has a sharp end adapted to pierce a soft tissue repair prosthetic and abdominal wall tissue. Each needle also includes a suture receiving channel. A suture is carried by the instrument. The suture is defined by a first segment and a second segment, the first segment is located in the first suture receiving channel and the second segment is located in the second suture receiving channel.

Another aspect of the invention is an instrument for delivering a transfascial suture including a handle and an elongated shaft extending from the handle, the shaft including a distal end. The instrument includes a first needle and a second needle, the first and second needles being moveable to an extended position beyond the distal end of the shaft. Each needle has a sharp end adapted to pierce a soft tissue repair prosthetic and abdominal wall tissue. The instrument includes a plurality of sutures indexed according to a delivery sequence, and is configured to register a next indexed suture in the delivery sequence with the first and second needles.

Another aspect of the invention is an instrument for delivering a transfascial suture including a handle and an elongated shaft extending from the handle, the shaft including a distal end. The instrument includes a first drive member and a second drive member, the first and second drive members being moveable along respective drive paths to an extended position beyond the distal end of the shaft. The instrument carries a suture, the suture defined by a first segment and a second segment. A first suture retainer is connected to the first segment and is located in a first drive path, and a second suture retainer is connected to the second segment and is located in a second drive path, the first and second suture retainers being carried by the instrument.

Another aspect of the invention is a tip for a transfascial suture delivery instrument including a tip body having a first needle pathway and a second needle pathway. Each of the first and second needle pathways being registrable with a respective first needle channel and a second needle channel in a transfascial suture delivery instrument. The instrument includes at least one suture defined by a first segment and a second segment, the first and second suture segments, or a retainer associated with each of the first and second suture segments, being located along the first needle pathway and the second needle pathway, respectively. The tip body is adapted to removably fit to the transfascial suture delivery instrument with the first and second needle pathways registered with the first and second needle channels.

Another aspect of the invention is a tip for an instrument for delivering a transfascial suture including a tip body having a first needle pathway and a second needle pathway. Each of the first and second needle pathways have a portion adapted to register with a respective first needle channel and a second needle channel in a transfascial suture delivery instrument. The tip body includes at least one suture defined by a first segment and a second segment. An elongated suture enclosure extends proximally of the first and second pathways, the first and second segments being located within the elongated suture enclosure. The tip body is adapted to fit to the transfascial suture delivery instrument with the first and second needle pathways registered with the first and second needle channels.

Another aspect of the invention is a suture assembly including a suture having a first segment, a second segment, and an intermediate section between the first segment and the second segment. A first suture retainer is connected to the first segment, and a second suture retainer is connected to the second segment. A suture force distributing member is positioned about the intermediate section.

Another aspect of the invention is a suture assembly including a suture and a suture retainer. The suture retainer includes a connector to connect with the suture. The position of the connector being selectively adjustable along the length of the suture. The suture retainer includes an axial bore therethrough for receiving a needle.

Another aspect of the invention is an instrument for delivering a transfascial suture including a handle and an elongated shaft extending from the handle, the elongated shaft including a distal end. A needle extends through the elongated shaft and is advanceable beyond the distal end, the needle including a sharp tip and a drive feature. A plurality of suture retainers are stacked in an end-to-end orientation on the needle, each pair of suture retainers connected to a single suture. A stop is provided at the distal end, the stop adapted to be overcome by needle induced movement of the distal-most suture retainer. The drive feature has a firing profile to drive the distal-most suture retainer through the stop and out of the distal end when the needle is moved in the distal direction, and a reloading profile allowing the drive feature to move past the next distal-most suture retainer as the needle is moved in the proximal direction.

A still further aspect of the invention is an instrument for delivering a transfascial suture including a handle, an elongated shaft extending from the handle, the shaft including a distal end. A pair of needles extend through the shaft and are advanceable beyond the distal end. The instrument includes a pick-up area and a loading zone in the distal end. A suture including a force distribution member is located in the pick-up area, and one or more sutures each including a force distribution member are located in the loading zone. A translating feature moves a suture and force distribution member from the loading zone to the pick-up area.

BRIEF DESCRIPTION OF DRAWINGS

The foregoing and other objects and advantages of the invention will be appreciated more fully from the following drawings, wherein like reference characters designate like features, in which:

FIGS. 2-5D are illustrations of an instrument for transfascial delivery of a suture;

FIGS. 9-13 are illustrations of an instrument for transfascial delivery of a suture including a reusable unit and a disposable tip;

FIGS. 16A-21B are illustrations of various suture retainers;

FIGS. 22-25C are illustrations of an instrument for transfascial delivery of a plurality of sutures;

FIGS. 26A-27 are illustrations of an instrument for transfascial delivery of a plurality of sutures;

FIGS. 29-32C are illustrations of an instrument for transfascial delivery of a plurality of sutures;

FIGS. 34-34D are illustrations of an instrument for transfascial delivery of a suture assembly including a subcutaneous anchor.

DETAILED DESCRIPTION

Figure 1:
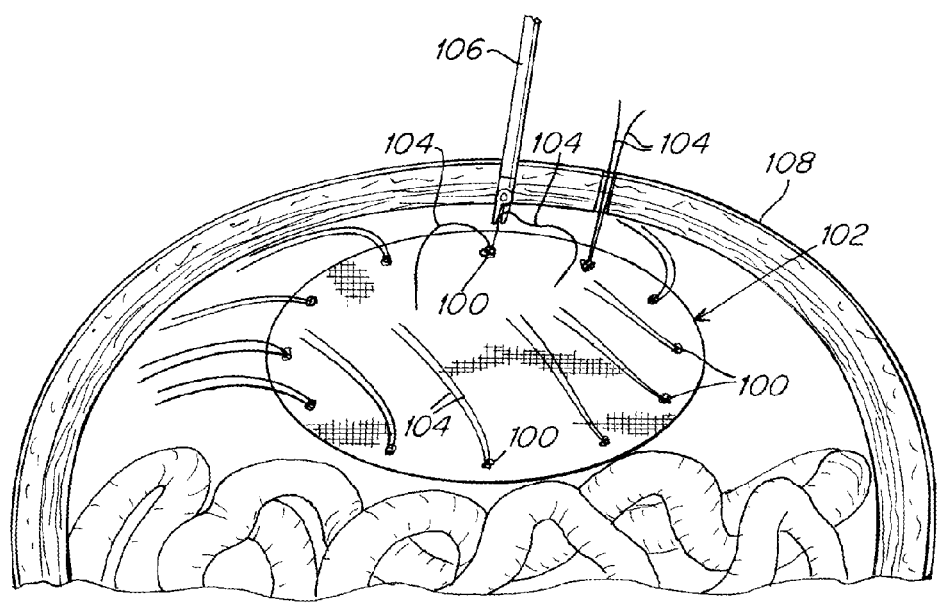
FIG. 1 is an illustration of a conventional transfascial suture delivery.
Figure 2:
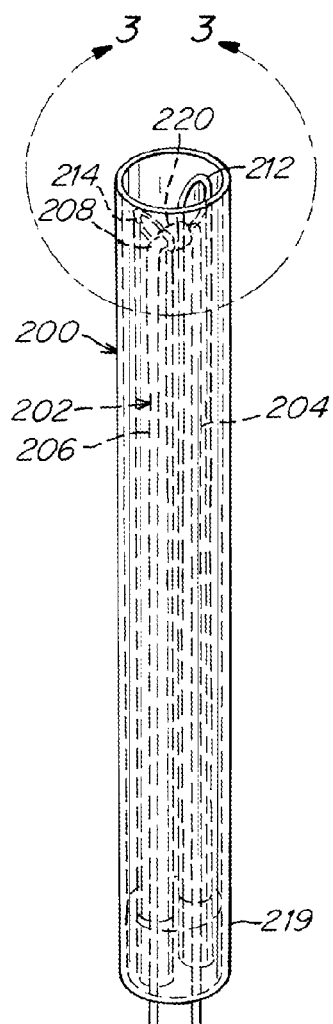
Figure 3:
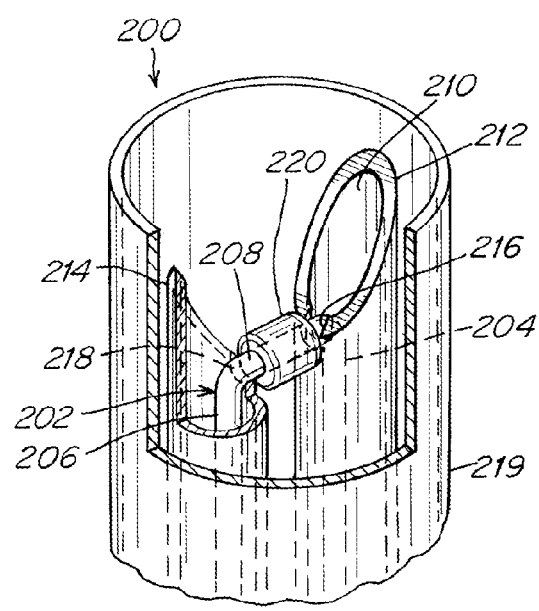
Figure 4:
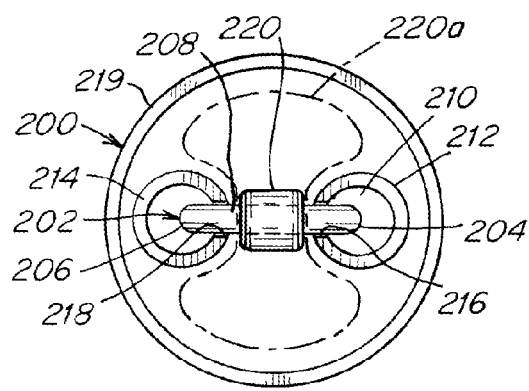

Various aspects of the invention are described below and/or shown in the drawings. These aspects of the invention may be used alone and/or in any suitable combination with each other. Aspects of the invention are not limited in any way by the illustrative embodiments shown and described herein.

Embodiments of the invention are described in connection with instruments for transfascial delivery of one or more sutures, arrangements of transfascial suture assemblies, and methods of delivering a transfascial suture. These instruments, suture assemblies, and methodologies are particularly configured for transfascial delivery of sutures from within the abdominal cavity to the outside of the patient, rather than in the traditional manner of pulling sutures across the fascia in an approach from outside of the patient. Such instruments, suture assemblies, and techniques may be applied independently or in conjunction with other approaches, such as those involving mechanical fastener-type fixation. Although disclosed in connection with a repair of a ventral hernia, the invention is not so limited and has other applications as should be apparent to one of skill in the art.

An instrument for transfascial delivery of a suture may include an actuating handle, an elongated shaft extending from the handle, one or more sutures loaded in the instrument and a drive system for advancing the suture out of the instrument. The shaft may be flexible, may be configured with a selectively articulating tip, may be selectively rotatable, and may be sized to fit through a narrow cannula, such as a 5 mm cannula or even smaller—although the outer diameter of the shaft is not necessarily a limitation of the invention.

The drive system may include one or a pair of needles or other drive elements, each with an end configured for piercing tissue and/or a soft tissue repair prosthetic, such as a ventral hernia patch. A pair of drive needles may be arranged to move simultaneously or, instead, in sequence, and may be driven by a single or a dual actuating arrangement (e.g., one trigger or two triggers).

The instrument may have a non-piercing mode with a sharp end of each needle or other tissue piercing member being shielded against contact with abdominal wall tissue and a piercing mode with the sharp end of the needle being available for contact with abdominal wall tissue. The instrument may be inserted in the non-piercing mode into the abdominal cavity. After positioning adjacent the abdominal wall, the instrument may be actuated to the piercing mode, and the needle may be advanced through at least a part of the abdominal wall.

The one or more sutures may be in carrying engagement with the needles as-loaded, or may be positioned in a path of movement of the needles so that the suture is picked up and advanced out of the instrument by the moving needles. The suture may be arranged so that a first suture segment is associated with a first needle and a second suture segment is associated with a second needle, with an intermediate suture segment extending between the two. So arranged, deployment of the pair of needles will deliver both suture segments through a ventral hernia patch and then through fascial tissue, with the intermediate segment remaining in the abdominal cavity internal of the ventral repair patch. The portions of the first and second suture segments delivered through and beyond the patch and fascial tissue, referred to as suture tails or suture segment tails, may then be joined, such as by tying, and prior to joining may be pulled to draw the intermediate segment against the ventral repair patch.

A suture force distributing member may be provided along the intermediate segment of the suture, so that the force distributing member contacts the ventral repair patch when the suture tails are drawn away from the abdominal cavity and/or secured together. The suture force distributing member may be fixed in position on the intermediate segment or may 'float' along the intermediate segment.

Where a plurality of sutures are loaded in an instrument, an indexing system may be provided to deliver the sutures according to a predetermined sequence, and such indexing system may be axially based, rotationally based, or otherwise. The instrument may be arranged to provide for tangle-free storage of a plurality of sutures. Further, the instrument may be configured as a reusable device, a disposable device, or a hybrid including a reusable aspect and a disposable aspect. Such a hybrid device might include, for example, a reusable handle and shaft and a disposable tip and suture assembly that is mountable to the shaft. A safety mechanism may be provided to prevent firing of the needle when no sutures are present, or are not properly loaded, in the instrument. The instrument and suture assemblies preferably will be sterilized prior to transfascial suturing.

One embodiment of a transfascial suture delivery instrument 200 is illustrated in FIGS. 2-5D (handle is not shown) and is arranged to deliver a suture 202 defined by a first segment 204, a second segment 206 and an intermediate segment 208. The first segment may be positioned within the channel 210 of a needle 212 or otherwise contained within the needle. The second segment may be similarly positioned with respect to the second needle 214. Locating the first and second suture segments within the first and second needles may allow for a reduced instrument profile. However, the suture segments could be positioned externally of the needles (anywhere about the circumference of the needle including between the needles), or partially internal of the needles and partially external of the needles. For example, and without limitation, the suture segments could extend across each, respective, needle tip and then run along opposite sides of the needle bodies. Further, the suture segments may be extended partially or fully lengthwise, that is essentially or partially linearly, or may be partially or fully reduced in length such as being in the form of loops or coils. In any of such arrangements, it is preferable to load and deliver the suture segments in a fashion that minimizes tangling. The internal or external surface of the needles may be coated or otherwise finished to facilitate delivery of the suture segments without damaging the suture.

The tips of each of the needles may be pointed to facilitate piercing of a ventral repair patch P and/or abdominal wall tissue W. The needles may include a notch 216, 218 or other feature to assist in picking up and/or paying out the suture segments as the needles are deployed. The as-loaded suture may be in an inverted U-shaped configuration as shown, with the tail ends of the suture segments being closer to the proximal end of the shaft 219. Consequently, when the needles are deployed from a non-piercing mode, as shown in FIG. 5A, to a piercing mode, as shown in FIG. 5B, the portions of the suture segments closer to the intermediate segment are first delivered from the instrument with the portions of the suture segments closer to the tail ends, or the tail ends themselves where the entire suture segments are released from the instrument, being delivered later. After deployment, respective suture tail pairs may be knotted, excess suture length trimmed, and the skin over the suture knot closed by stitching, adhesive strip or otherwise, as shown in FIGS. 5C-5D.

A force distributing member 220 may be provided along the intermediate segment of the suture, and may be located between the needles in the as-loaded arrangement as shown or may be moved into position between the needles at a point during needle deployment. The force distributing member may be fixed in position to the suture or may be freely moveable along a length of the suture (i.e., floating). In a fixed embodiment, the force distributing member may be joined to the intermediate segment through mechanical arrangements, such as by crimping the force distributing member to the segment or by one or more clamps or wedges provided in the force distributing member that may be engaged to the segment. Alternatively, and again without limitation, the suture may be tied to the force distributing member to fix the position at the intermediate segment. Additionally, the force distributing member may be joined by thermal or chemical bonding with the suture, by heat shrinking the force distributing member to the suture, or by an adhesive applied between the two components. Further, the force distributing member may be integrally formed with the suture, such as by hardening or reshaping a portion of the suture. The force distributing member is not limited to the tubular shape shown, as should be apparent to one of skill in the art, and may have other configurations such as a substantially plate-like or planar arrangement (including, without limitation, flat, slightly convex, slightly concave, and hybrids of the foregoing) with such substantially planar embodiments including any design suitable for spreading forces applied along the suture. An alternative arrangement is an hourglass or bow-tie configuration (shown as 220*a* in FIG. 4) with openings therethrough, or along contoured edges, for passage of the suture segments. Other three-dimensional and substantially planar shapes, as well as compound shapes including three-dimensional and planar aspects, are contemplated as one of skill in the art will appreciate. Further, one or more surfaces of the force distributing member may be adapted for contact or engagement with the soft tissue repair prosthetic. For example, a tubular shaped force distributing member may include one or more specially shaped surfaces, or facets, about its circumference, which may be planar, convex, concave, or other arrangement suitable to promote contact or engagement between the force distributing member and the soft tissue repair prosthetic. The force distributing member may be formed of a permanent material (e.g., polypropylene, polycarbonate, nylon, polyester, stainless steel, titanium), an absorbable material (e.g., polyglycolic acid (PGA), polylactic acid (PLA), polydioxanone (PDO), and blends of any of the foregoing), or a hybrid of a permanent material and an absorbable material.

Figure 6:
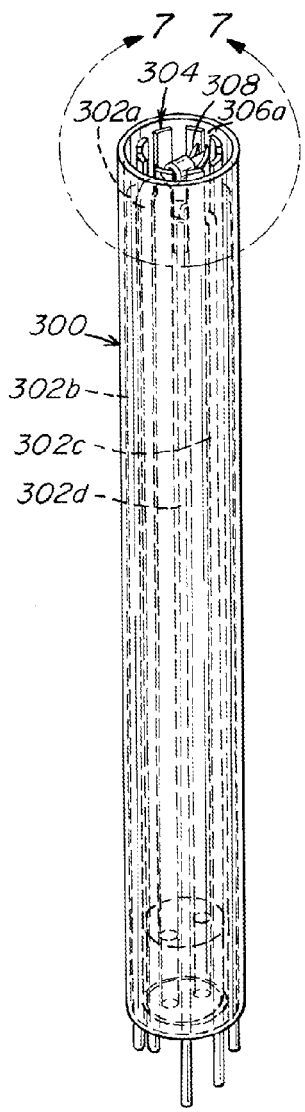
FIGS. 6-8 are illustrations an instrument for transfascial delivery of a plurality of sutures.
Figure 7:
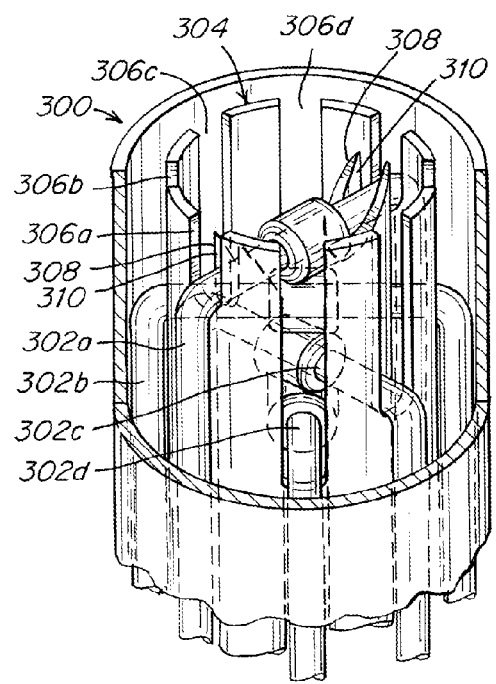
Figure 8:
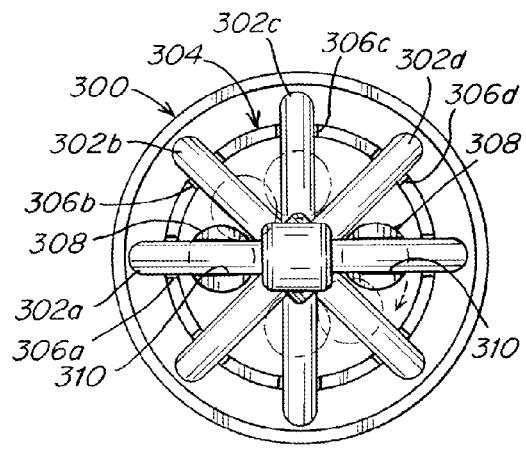

A transfascial suture delivery instrument 300 arranged to deliver a multiple of pre-loaded sutures 302*a-d* is illustrated in FIGS. 6-8. The sutures may be in a form similar to the suture described in connection with FIGS. 2-4, characterized by a first segment, a second segment, and an intermediate segment to which a force distributing member may be provided. The sutures may be indexed in an intended delivery sequence. In the axial index shown, the distal-most suture 302*a* will be delivered first, the next distal-most suture 302*b* will be delivered second, with the indexing continuing in this fashion along the length of the stack.

An inner cannula 304 may be provided with pairs of slots 306*a-d* of varying length corresponding to respective positions in the index order. For example, the distal-most suture may be located in a pair of slots which is located closest to the distal tip of the instrument and, consequently, the pair of slots associated with the distal-most suture have a length shorter than the pair of slots for the next distal-most suture.

The axial indexing arrangement may be reversed so that the distal-most suture is the last suture delivered by the instrument and, further, other delivery sequences for an axial stacking arrangement may be employed as should be apparent to one of skill in the art. The indexing sequence also, or alternatively, may be characterized by rotational positioning about the circumference of the inner cannula. For example, the first suture may be located at a reference location, and then the second suture in the sequence located at a predetermined angular adjustment from the reference location (i.e., first suture), and then the third suture at a further angular adjustment from the second suture. The angular adjustments may be the same or varying as between different suture positions in the indexing sequence. For example, and without limitation, the angular adjustment between different suture index positions (e.g., pairs of slots) may be 30 degrees, allowing 6 different sutures to be indexed for a single circumferential indexing arrangement. As a further example, also non-limiting, a rotational offset of 45 degrees would permit circumferential indexing of 4 sutures, as shown in FIGS. 6-8.

As shown, the sutures are indexed axially and rotationally, with the first and second segments of each suture hanging over and draped along the outer surface of the indexing cannula, with the intermediate segment, with or without a force distributing member, extending across and internally of the indexing cannula. The indexing cannula may include outer partitions, ribs, or other features to maintain the separateness of the suture segments and avoid tangling therebetween. As described above and shown, the suture segments may be fully extended in a lengthwise direction or may be partially or substantially completely reduced in length, for example by being looped into coils. If desired, the indexing cannula may include an outer wall that shrouds the suture segments, and such an arrangement may facilitate assembly and insertion of a suture loaded indexing cannula into the instrument. One or more of adjacent, axially stacked, intermediate segments may be spaced from each other or, alternatively, may be in contact.

A pair of needles 308 are advanceable to deliver each suture from the instrument in the desired indexing sequence. The needles may be located within the indexing cannula, or otherwise arranged to pick-up or carry a suture from within the indexing cannula, as shown. Alternatively, the needles may be located externally of the indexing cannula or otherwise arranged to pick-up or carry a suture externally of the indexing cannula.

The needles may be adapted for piercing the soft tissue repair prosthetic and fascial tissue, and may include one or more features adapted to pick-up and pay out the suture segments as the needles are deployed, for example, the notched 310 arrangement shown. The needles may be solid or hollow, as the structure of the needles is not necessarily a limitation of the invention as should be apparent to one of skill in the art.

The stroke of the needles may be coordinated with the indexing location of the sutures. For example, in certain embodiments where the sutures are stacked axially, the needles must be retracted far enough to reach the proximal-most suture in the index. The stroke length in these particular embodiments, then, must be designed to reach the proximal-most suture for each retraction of the needle. Alternatively, in other axial indexing embodiments, the stroke length may be dynamic and vary depending upon the sequence order of the suture being delivered.

The needles may be rotated a predetermined angular adjustment corresponding to the next suture position in the index, and such rotational indexing may occur automatically in response to actuation of the instrument, such as at the end of the backstroke of the prior suture delivery or at some other interval, or may occur manually, as should be apparent to one of skill in the art. Once rotated, the needles are reset to pick up the next suture in the sequence. Alternatively, the indexing cannula may be arranged to rotate, while the needles remain in the same orientation, whether automatically in response to actuation of the instrument, for example at the end of the backstroke of the prior suture delivery, at some other interval, or manually.

An instrument 400 for delivering a transfascial suture is shown in FIGS. 9-13 and includes a reusable unit 402 having a handle 404, an elongated shaft 406 and a drive assembly included within and actuatable at the handle, and a disposable unit 408 including a tip 410 and suture assembly 412. The reusable unit includes a pair of drive elements 414, which may be in the form of needles, that extend along the elongated shaft and are deployable and retractable in response to actuation of a control mechanism at the handle.

As shown, the path of the drive elements or needles may diverge, increasing the spacing between the needles beyond the instrument and the amount of tissue purchase thereby. Alternatively, the drive element paths may be parallel or converging. The drive elements may run on a surface of the shaft but, preferably, are located in one or a pair of channels 416 running through the shaft as illustrated.

The distal face of the shaft may include an exit opening of the respective channels through which the drive elements may extend when deployed. The surface of the shaft may be contoured 420, as shown, to cooperate with an interface feature 422 in the disposable tip and also may be adapted to receive a suture support 424, both described further below. Although shown with a truncated elliptical cross-section, the shape of the shaft is not so limited as should be apparent to one of skill in the art.

The disposable tip includes a body portion 426 with a distal extension 428 and a proximal extension 430. The proximal extension is shaped to mount about the distal portion of the shaft and includes an interface 422 for snap fitting into the complementary recess 420 in the shaft. The location of these complementary interface features could be reversed and other arrangements for releasably engaging the disposable tip to the shaft are contemplated as should be apparent to one of skill in the art.

In one embodiment, a releaseable interface between the distal shaft face and proximal face of the tip body may be provided, such as a male/female arrangement 432, 434 shown, which assist in the releasable connection between the two components and may be in lieu of the proximal extension and shaft interface. The tip body includes a pair of drive channels 436 with openings that are registrable, respectively, with the first and second exit openings in the distal face of the shaft. The distal extension includes a pair of drive paths 438 that continue from the drive channels extending through the tip body. Wall structure may be built up around, and/or between, the drive paths to guide and/or support the drive elements.

Extending proximally of the tip body is a support 424 for a pair of suture segments. The support may be tubular shaped and may be integral with the proximal extension or a separate component that extends from the tip body along the extension, whether internal of the extension as shown, or external of the extension if desired. The suture support may form a single channel or may be divided, fully or partially, or otherwise configured to maintain first and second suture segments separate from each other. The support is arranged to mount to the shaft, such as by seating in a complementary recess 440 formed in the shaft surface. As shown, the complementary recess may be in the form of an elongated concave depression, bounded by convex walls. Other arrangements of a mount for the suture support are contemplated and this particular configuration is not necessarily a limitation of the invention. The suture support communicates with an opening through the tip body which may include a mount 442 or support for a force distribution member 444, such as the washer-type device shown. The opening may include a divider presenting a first segment opening and a second segment opening.

A suture retainer 450 may be located in each of the drive paths, with each retainer connected to one of the suture segments 452 extending through the opening or openings in the tip body. The suture retainers are adapted to receive and be carried by the drive elements as they are advanced from the shaft of the reusable unit, through the tip body and along and beyond the distal extension of the tip. In one embodiment, the suture retainers each include an axial through-bore for receiving a portion of a needle tip. The bore and/or needle may be configured so only part of the needle will project through the retainer. For example, and without limitation, the needle may include a necked down narrow tip portion that is extendable through and beyond the retainer bore, and a stepped up larger proximal portion that is engageable with the retainer, for example with an internal or external shoulder of the retainer.

As shown, the force distribution member may be arranged in floating relationship with the suture segments; that is, the force distribution member need not be fixedly located at a singular position on the suture. After both suture segments are fully deployed out of the instrument, whether by advancement of the needles or by pulling of the suture tails or tail segments that have been transfascially delivered, the force distributing member and intermediate segment will position against the soft tissue repair patch. Prior to full deployment, the force distribution member may stay with the disposable tip or may be suspended by the moving suture segments even though displaced from the instrument.

The suture retainers are carried by the needles from the instrument through the soft tissue repair prosthetic and/or fascial tissue, presenting on the other side of the abdominal wall. Upon completion of the instrument stroke, the needles retract back through the fascia and abdominal wall patch, leaving a first suture segment running from a first suture retainer located exterior of the abdominal cavity, to an intermediate segment and force distribution member internal of the abdominal cavity and positionable against the abdominal wall patch, and back to a second segment running from the force distribution member through the abdominal wall patch and fascia to a second retainer located exterior of the fascia. The deployed retainers may be reoriented, automatically or manually, so that the retainers are unlikely to slip back through the needle puncture openings. The retainers hold the suture segments in place pending tying, or other securing, of the suture tails together. The retainers may be left as deployed, pending delivery of other sutures about the abdominal wall patch, or the surgeon may choose to tie or otherwise connect the ends of each pair of suture tails prior to delivering the next suture. Prior to tying together or other connection of the suture tails, the suture segments may be pulled to take up any excess suture slack still remaining in the instrument or in the abdominal cavity, preferably while holding the suture retainers against the patient. Where the soft tissue repair patch is not already positioned flush against the abdominal wall, such retraction of the suture segments may help hoist a portion of the patch into position.

Figure 14:
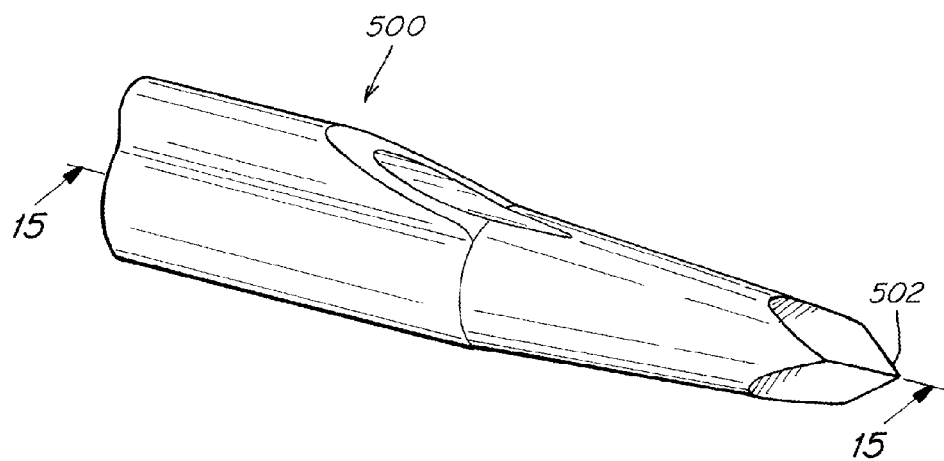
FIGS. 14-15 are illustrations of a suture retainer with a tissue piercing tip.
Figure 15:
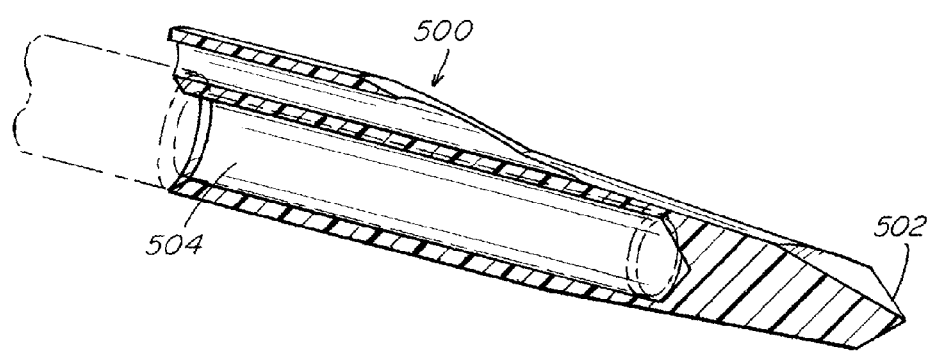

Although just described with an axial-through bore for receiving a needle, the suture retainer may have a different arrangement, as shown in FIGS. 14-15, where the suture retainer 500, itself, is formed with a tip 502 that is sharp and otherwise adapted to pierce the abdominal wall prosthesis and/or abdominal wall. In this embodiment, then, the suture retainer does not have to be configured to extend a needle therethrough, and may be solid or include only a partially extending axial-bore 504. The tip of the drive elements will be configured to appropriately engage with and advance such alternatively designed suture retainers. For example, and without limitation, the suture retainer may include a partial axially extending bore, and the drive element may include a cylindrical portion that is compatible and just slightly narrower than the bore so as to fit within and be removable from the bore without catching. For a solid suture retainer, the proximal face may include features such as notches or projections, or other arrangements, that provisionally engage with complementary features in the distal end of the drive element.

Various suture retainer arrangements are shown in FIGS. 16A-21B. A suture retainer 600 may include a tapered distal end 602 to assist in advancement through the soft tissue repair prosthetic P and the fascial tissue W. A proximal portion 604 may be wider than the distal end, making it more difficult for the suture retainer to pass back through the puncture formed through the fascia and abdominal wall prosthesis, and such enlargement may be symmetrical or asymmetrical. In certain embodiments, the proximal portion includes a side body 606 that extends radially from the main retainer body. The side body may be tubular shaped, or at least present a curved outer wall, and have a distal portion 608 that tapers towards the retainer body. The side body may serve as a connector between the retainer and the suture segment.

In the embodiment of FIGS. 16A-16B, the suture segment is fixed at the connector such as by insert molding, adhesive or ultrasonic bonding sections of the connector about an end of the suture segment, mechanically clamping or otherwise mechanically securing the end of the suture segment to the connector, or other approach as should be apparent to one of skill in the art. Alternatively, the connector may be configured to allow the suture segment to move therethrough, so that the location of the suture segment within the connector is selectively variable. In such cases, an end of the suture segment may be knotted, formed in a bulbous shape, or otherwise configured so as not to pass through the connector, preventing the suture segment from slipping out. Although described as a substantially tubular side body, other configurations of a connector for a suture segment are contemplated as should be apparent to one of skill in the art.

As illustrated in FIGS. 17A-21B, the connector may include an axial bore 610 extending at least partially through the connector.

The axial bore may open 612 transversely through the connector sidewall, as shown in FIGS. 17A-17B, and include a wedge or other suture lock arrangement that is actuated by pulling the suture segment axially through the connector and then over the connector and back in the direction of the proximal end. Where there is tension on the suture segment, the already delivered suture retainer may stand upright against the fascia.

A portion of the connector at a proximal end may include a side-cut 614, as shown in FIGS. 18A-18B, or other arrangement that allows the suture retainer to tip over and lay transversely to the direction of the suture segment (e.g., flat against the fascia) that has escaped through the side-cut. Here, again, a wedge or other suture locking feature may be incorporated in a transverse opening in the connector sidewall.

In a further embodiment illustrated in FIGS. 19A-19B, a tipping arm 616 may extend from the connector or other aspect of the retainer, about which the suture segment may be wrapped to encourage tipping of the retainer.

Figure 20A:
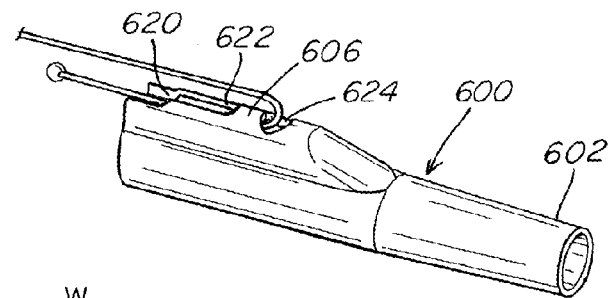
Figure 20B:
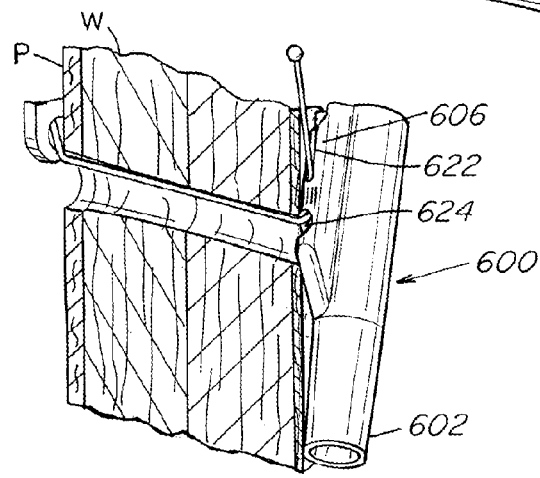

In an arrangement shown in FIGS. 20A-20B, a connector includes an axial bore 620, a first opening 624 through the connector sidewall and a second opening 622 in the connector sidewall, in the form of a slot, spaced from the first opening and extending in the same direction through the connector sidewall. A suture can be arranged to run through the connector so that the enlarged tail end can be pulled in a direction away from the proximal end of the retainer and then cinched against the suture lock in the slot.

Figure 21A:
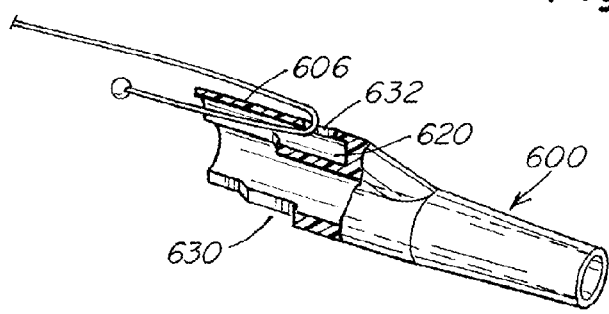
Figure 21B:
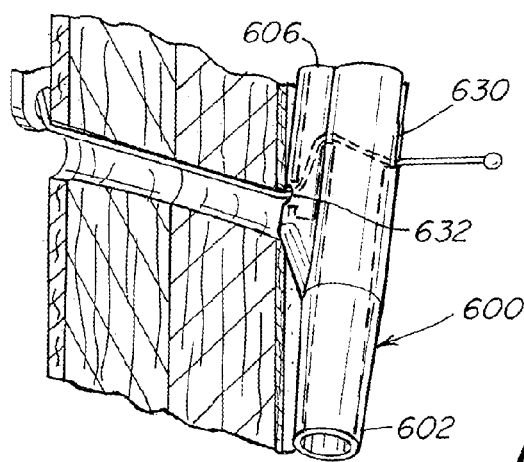

In a variation shown in FIGS. 21A-21B, a slot 630 may open in a direction transversely to a first opening 632 in the connector sidewall so that the tail may be pulled through the slot and away from the retainer in a first direction and the remaining suture segment can extend from the first opening in a generally opposite direction.

Other arrangements of connectors for suture retainers, particularly the arrangements of openings and/or slots to facilitate orientation of a suture retainer relative to the fascia, are contemplated as should be apparent to one of skill in the art. For example, and without limitation, the sidecut, slot and/or opening may including varying directional components to allow relative positioning of the suture retainer and suture tail, so that the suture retainer may be rotated as well as tipped over. Further, although each end of a suture has been described as being associated with a respective suture retainer, the invention is not so limited and only one end of a suture need be employed with a suture retainer. In this latter embodiment, the other end of the suture may be attached to a different component, such as a T-bar fastener, or may be free of any additional component.

An instrument for delivery of transfascial sutures 700, shown in FIGS. 22-25C, is pre-loaded with a plurality of sutures. Each suture includes a first suture segment attached to a first suture retainer 750, a second suture segment attached to a second suture retainer 750, and an intermediate segment extending therebetween which may further incorporate a force distribution member.

The instrument includes a handle 702, an outer shaft 704, and a single drive needle 706 located within the outer shaft about which the suture retainer pairs are mounted in end-to-end fashion. Adjacent suture retainers may be slightly spaced from each other, or in contact. A proximal end of the drive needle may extend outside of the handle and may be pushed forward to drive the tip of the needle to a deployed position beyond the end of the shaft. The proximal end of the drive needle may then be retracted to reposition the needle tip at a starting position. Other arrangements for deploying and retracting the drive needle are contemplated as should be apparent to one of skill in the art.

A biased loading member, such as a spring ending in a washer or other structure is adapted to act against a proximal end of the retainer stack, urging the retainer stack towards the distal tip. A resilient stop 708 extends inwardly from the shaft preventing further displacement of the stack in response to the biased loading member. Slightly more than a retainer's length proximal of the distal tip, sufficient to account for projection of the piercing tip of the needle through the retainer, the drive needle includes an active drive and reload feature 710. The drive and reload feature is biased into a drive profile to engage a distal-most retainer as the needle is deployed, imparting a drive force to the distal-most retainer that overcomes the resilient stop and forces the retainer through the puncture path in the abdominal wall patch and fascia that has been formed by the deploying needle.

As the needle retracts through the shaft on its return stroke, the active drive and reload feature contacts the tip of the next suture retainer, which has been advanced to the stop by the biased loading member. The rearward force on the active drive and reload feature as it contacts the tip of the next suture retainer overcomes the bias for the drive profile, causing the drive and reload feature to move into a reloading profile that is adapted to pass through the retainer. Upon completion of the stroke, the drive and reload feature emerges proximal of the new distal-most retainer and biases again into the drive profile.

In one embodiment, the active drive and reload feature includes a cam member that is pivoted to the drive needle so that forces directed against the front of the cam member cause upward pivoting into a drive profile, while forces directed to the back of the cam member cause downward pivoting into a reloading profile. As shown, and but one example of a drive and reload feature, is a wedge shaped member pivotally mounted to the drive needle with an upright front face 712 and a downwardly inclining back face 714.

An instrument 800 for delivering transfascial sutures is shown in FIGS. 26A-27 and includes a plurality of preloaded suture and suture force distribution members 802a-f. The delivery instrument includes an elongated shaft 804 and a pair of needles 806 or other drive elements which may be configured similar to the needles and drive elements previously described so as to be controllably moved through the instrument to pick up a pair of suture segments and transfascially deliver the suture and suture force distribution member. A distal end of the shaft includes a loading zone 810 and a pick-up position 812 for the suture and suture force distribution members. The loading zone may be arranged at a first side of the shaft with the pick-up position on another, preferably opposite, side of the shaft, with the needles or other delivery elements moveable through the pick-up position side of the shaft. The loading zone may include stacking walls, ribs or other features, projecting inwardly from the shaft, and that may be configured to correspond with the contour of the suture force distribution members to assist in aligning and guiding the position of the stack within the shaft.

The loading zone and pick-up position may overlap to some extent as shown in FIG. 27, such that a portion of the suture force distribution member in the pick-up zone may eclipse a portion of the next distal-most suture force distribution member. A design factor for relative location of the pick-up position and the stacking zone includes providing a clear path for the needle pairs to travel through the pick-up position so as to grab the suture segments.

In the loading zone, the suture and suture force distribution members may be stacked, such as in a face-to-face orientation as shown and be biased by a spring drive towards the distal tip of the instrument. Advance of the stack towards the distal tip is shown in FIG. 26D. The distal-most suture and suture force distribution member is moved, manually or automatically, to a pick-up position that is offset from the rest of the stack as shown in FIG. 26D. For example, and without limitation, a leaf spring, a cam element 814 formed or provided within the shaft and that cooperates with the spring drive, or other mechanical arrangement may be located at the distal end of the loading zone to bias over the distal most suture force distribution member into the pick-up position after the needle pair have been retracted proximal of the pick-up position. Other arrangements for translating, or otherwise moving, the suture force distribution member and associated suture segments to the pick-up position may be employed as should be apparent to one of skill in the art.

The pair of needles or other delivery elements are advanced to and through the pick-up position, picking up the suture segments and dragging the suture segments through the tissue as the needle is advanced well beyond the end of the instrument. The suture force distribution member, similar to previous embodiments, may be fixed to the suture segments or free-floating therealong. This delivery instrument is not limited to the shape or arrangement of the suture force distribution members shown nor to the position of the suture segments relative to the suture force distribution members. Other arrangements and configurations of sutures and suture force distribution members for use with a delivery instrument with attributes as just described are contemplated as should be apparent to one of skill in the art.

In an alternative embodiment, a cartridge separate and apart from the delivery instrument may similarly be loaded with one or more sutures and suture force distribution members and configured to receive the tip of the separate delivery instrument to load a suture and suture force distribution member. The delivery instrument, now loaded with a suture and suture force distribution member, may be removed from the cartridge and inserted through a cannula or narrow incision into the abdominal cavity and applied to fire the suture transfascially. The depleted delivery instrument may be withdrawn from the cavity and reloaded by again inserting the tip of the delivery instrument into the cartridge and picking-up the new distal-most suture and suture force distribution member. As with the integrated delivery instrument and cartridge arrangement described previously, the separate cartridge may be configured to translate, or otherwise move, the suture force distribution member from the stacked loading position to the pick-up position, with a leaf spring, cam, or other arrangement moving the suture force distribution member to the pick-up position once the needle pairs have vacated the pick-up position.

Figure 28A:
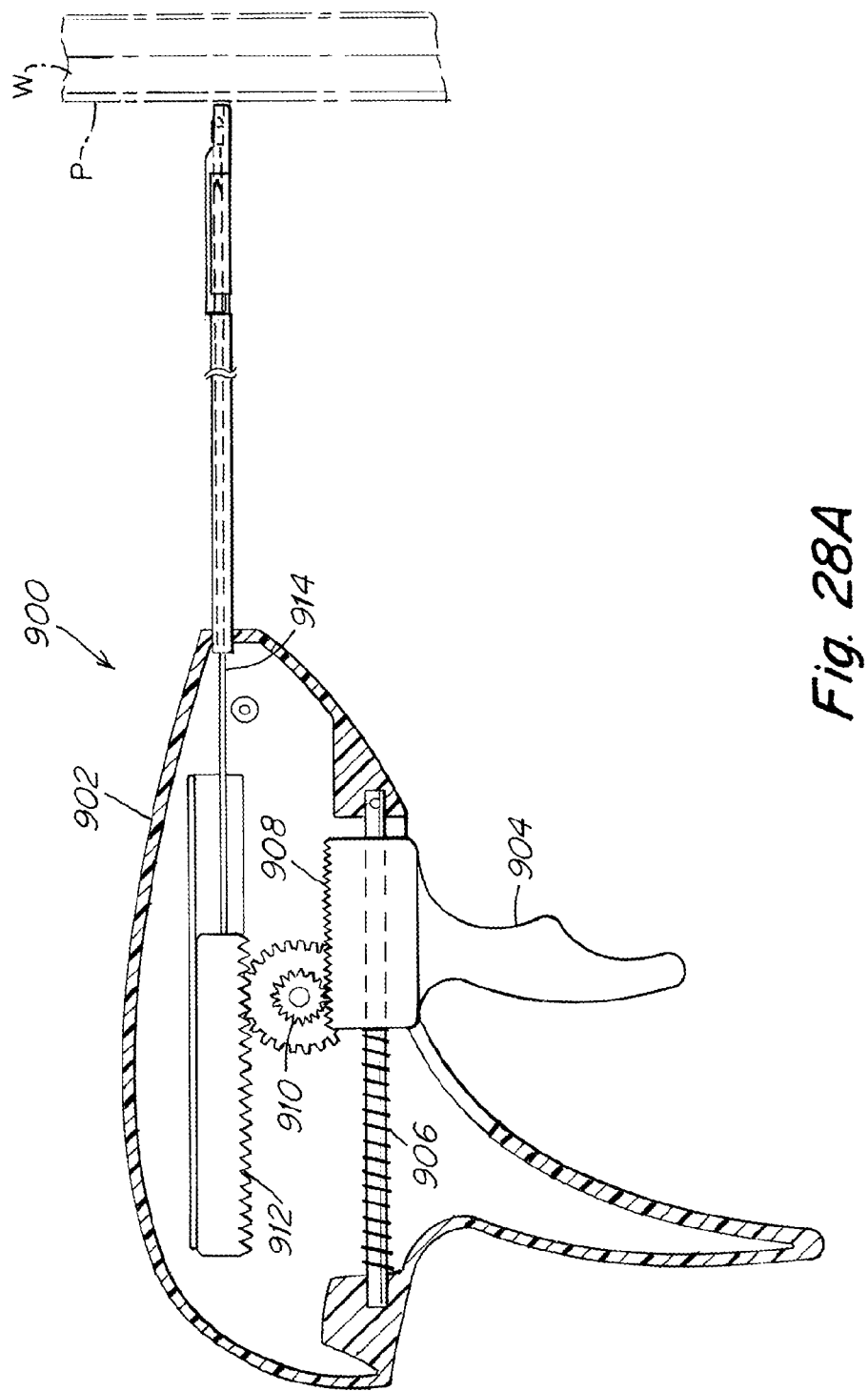
FIGS. 28A-28B are partial sectional illustrations of a drive mechanism for an instrument for transfascial delivery of a suture.
Figure 28B:
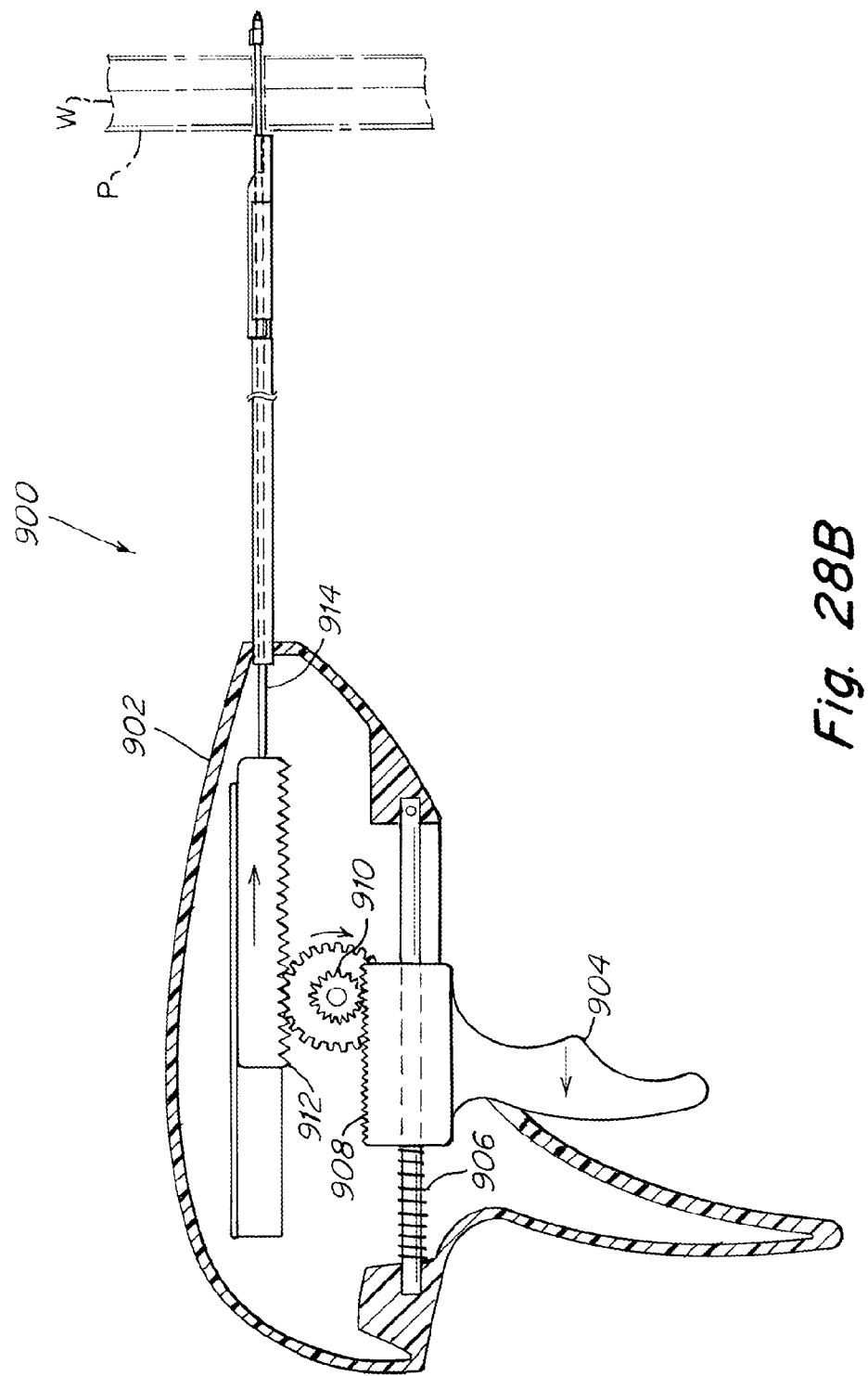

A system 900 for actuating the needles or other drive elements of a delivery instrument is shown in FIGS. 28A-28B and includes a handle body 902 which may be formed of a pair of handle sections as illustrated and which supports a rack and pinion drive system. A trigger 904 is mounted for linear movement along a bar and is translatable against the force of a spring 906 mounted about the bar towards the rear of the handle. A rack 908 governed by the trigger cooperates with a drive aspect 910 of a pinion gear to rotate the pinion gear in response to movement of the trigger. A separate rack 912, linked to a pair of needles 914 or other drive elements, moves in response to the rotation of the pinion gear, either towards the distal direction of the instrument so as to advance the needles or other drive elements out of the device, or in the proximal direction to retract the needles or other drive elements back into the shaft.

The handle body may include various mounts and support for the active components including, without limitation, a support for the needle rack, stabilizer rods for the needles, a pinion/drive gear mount, and a limit for distal movement of the trigger block. A pawl or other approach for providing incremental movement of the trigger may be incorporated into the handle arrangement. Incremental movements of the drive system may be coordinated to particular aspects of the suture delivery process. For example, and without limitation, the trigger stroke may have predetermined stopping points, such as at suture pickup or at various stages of needle deployment, allowing the physician to ensure it is appropriate to proceed to the next aspect of the stroke. Although an axial translatable trigger is shown, other arrangements including a pivoting trigger, and other actuators for a drive system, may be employed as should be apparent to one of skill in the art. Further, the rack and pinion drive system illustrated and described is but one of many drive systems that may be used to advance and retract the needle pairs or other drive elements of the delivery instrument.

An instrument for delivery of transfascial sutures 1000, shown in FIGS. 29-32C, may be pre-loaded with a plurality of sutures. Each suture includes a first suture segment attached to a first suture retainer, a second suture segment attached to a second suture retainer, and an intermediate segment extending therebetween which may further incorporate a force distribution member, if desired.

The instrument includes a hollow drive needle 1002 that may be located within an outer shaft (not shown) similar to those described above. An actuation handle, also similar to those described above, may be provided at a proximal end of the shaft to actuate the instrument for deploying sutures.

Suture retainer pairs 1004 are supported within the needle in end-to-end fashion. Adjacent suture retainers may be slightly spaced from each other, or in contact. The instrument may be configured to advance the stack of suture retainers along the length of the needle and deploy a distal-most suture retainer from the distal end of the needle in response to actuation of a control mechanism at the handle.

Figure 32:
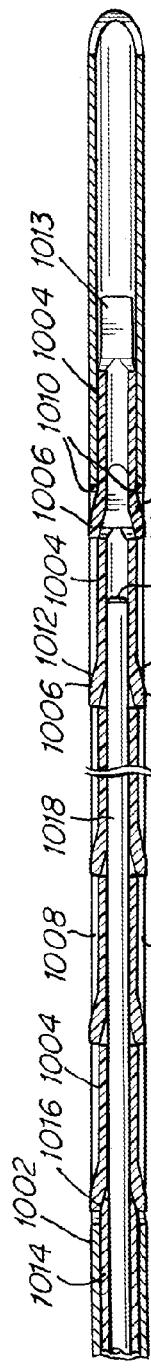

Each suture retainer 1004 may include one or more features that cooperate with the needle 1002 to maintain the suture retainers in the stacked configuration within the needle while also permitting the retainers to be moved along the length of the needle for controlled deployment. In one embodiment shown in FIGS. 29-31, each suture retainer 1004 may include a pair of protrusions 1006, such as fingers, that extend in an outward direction from opposing sides at a proximal end of the retainer and ride along elongated slots 1008 extending along opposite sides of the needle. The fingers are configured to protrude into the slots and eventually engage with a distal end 1010 of each slot when a suture retainer is advanced to a distal-most stack position within the needle. In this manner, as shown in FIG. 32, the distal-most suture retainer in the stack is restricted from advancing beyond the distal-most stack position along the needle when its fingers 1006 engage the distal ends 1010 of the slots 1008 to thereby retain the stack of suture retainers within the needle.

The suture retainers 1004 may be adapted to release from the needle upon application of a longitudinal force that is sufficient to overcome the engagement between the fingers 1006 of the distal-most retainer and the distal end 1010 of the slot. In one embodiment, each finger may include a cam surface 1012 that coacts with the end of the slot to deflect and collapse the finger inwardly as the longitudinal force is applied to drive the suture retainer in the distal direction. As shown, the cam surface 1012 may be angled outwardly from the retainer in a proximal direction. As shown in FIGS. 30-31, the distal portion of each retainer may be configured with a relief 1013, such as a slot, to receive the fingers of the adjacent retainer as the fingers become collapsed during a deployment sequence. Such an arrangement may allow for a more compact device. However, it is to be appreciated that the retainer may employ any suitable arrangement to facilitate stacking and release of the retainers as should be apparent to one of skill in the art.

Figure 32A:
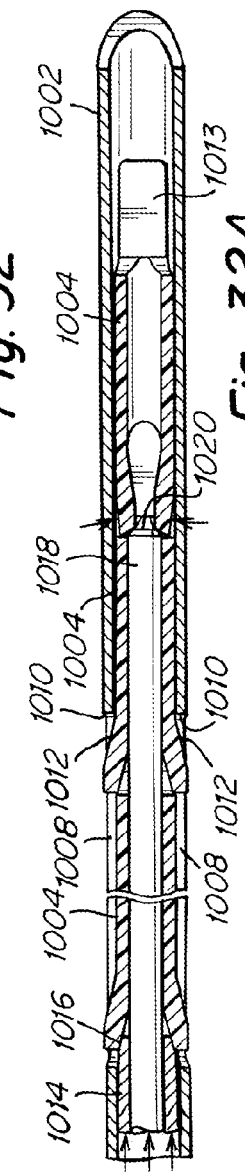

When the fingers 1012 are fully collapsed into a low profile, as shown in FIG. 32A, the distal-most suture retainer may be advanced distally beyond the distal-most stack position for deployment from the needle. The fingers may be resilient so that they return toward their original expanded position after deployment, making it more difficult for the suture retainer to pass back through the puncture formed through the fascia and abdominal wall prosthesis. However, use of a resilient finger is not a required feature and other engagement features may be employed as should be apparent to one of skill in the art. For example, and without limitation, the retainer may include shear pins or other deformable features that maintain the stack of suture retainers within the needle until deployment is desired.

A first pusher 1014 may be located within the shaft and be adapted to act against a proximal end of the retainer stack, urging the retainer stack towards the distal tip of the needle in response to actuation of the instrument. In one embodiment shown in FIGS. 30 and 32-32C, the first pusher 1014 may include a tube that is advanced along the length of the needle in response to actuation of the instrument. The first pusher may include a distal end 1016 that is configured to engage with a proximal portion of the most proximal suture retainer. Advancement of the first pusher in the distal direction applies a longitudinal force along the stack of retainers to advance the distal-most suture retainer into position for deployment from the needle. The first pusher 1014 may be configured to index the stack of retainers a distance corresponding to the length of a suture retainer so that only the distal-most retainer is released upon each stroke of the pusher.

Figure 32B:
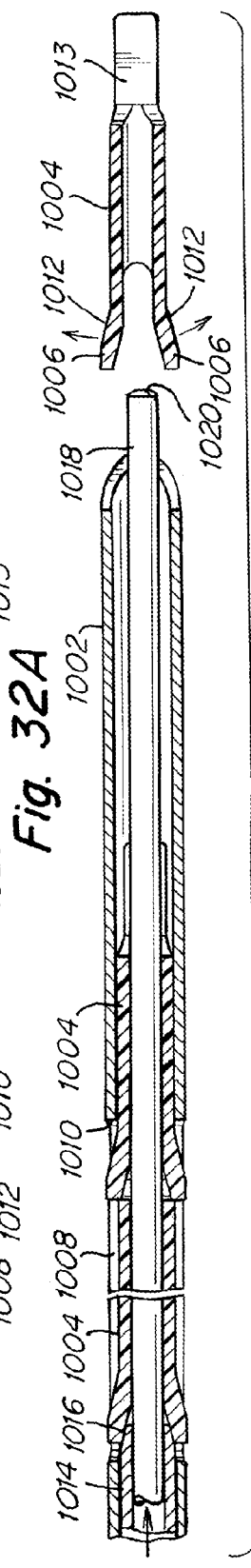

A second pusher 1018 may be located within the shaft and be adapted to drive the distal-most suture retainer from the needle in response to actuation of the instrument. In one embodiment, the second pusher 1018 may include a drive wire that is adapted to extend and retract in a reciprocating manner through the first pusher 1014 and the stack of suture retainers. As shown in FIG. 32A, the distal end 1020 of the second pusher is configured to engage with the collapsed proximal end of the distal-most suture retainer. Once engaged, distal extension of the second pusher 1018 drives the distal-most suture retainer from the needle, as shown in FIG. 32B.

Figure 32C:
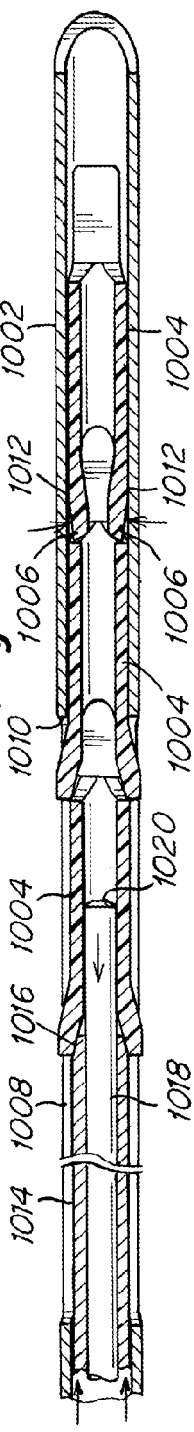

After deployment of the distal-most suture retainer, as shown in FIG. 32C, the second pusher 1018 is retracted proximally to its initial position for the next deployment sequence. The first pusher 1014 remains in its indexed position and engaged with the most proximal retainer in the stack to maintain the next distal-most suture retainer in position at the distal end of the slot for the next deployment sequence.

Although the instrument 1000 has been described above using one needle, it is to be appreciated that the instrument may include first and second needles with each needle supporting a stack of retainers 1004 arranged in end-to-end fashion. The instrument may be pre-loaded with a plurality of sutures with each suture including a first suture segment attached to a suture retainer in the first needle and a second suture segment attached to a correspondingly positioned suture retainer in the second needle. For example, and without limitation, the suture segments of a suture may be attached to the distal-most retainer in each needle. If desired, a force distribution member may be provided with the suture in a manner described above.

For some transfascial suturing procedures, it may be desirable to employ one or more suture retainers that may be deployed and/or implanted below the skin surface, for example, between the fascia and the dermal layer. An implantable suture retainer may be configured to anchor a suture or suture segment using a knotless procedure.

Figure 33:
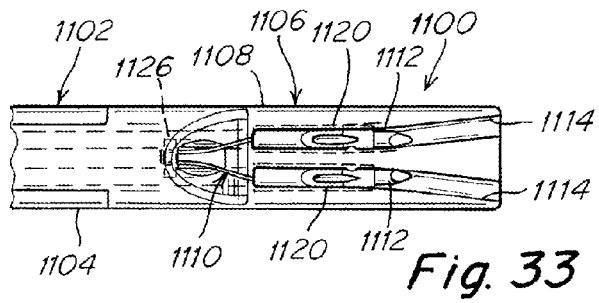
FIGS. 33-33C are illustrations of an instrument for transfascial delivery of a suture assembly including implantable retainers.
Figure 33A:
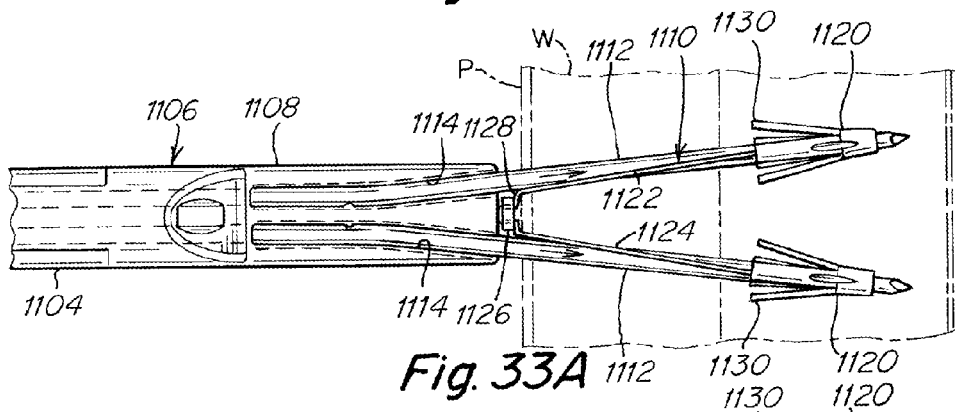
Figure 33B:
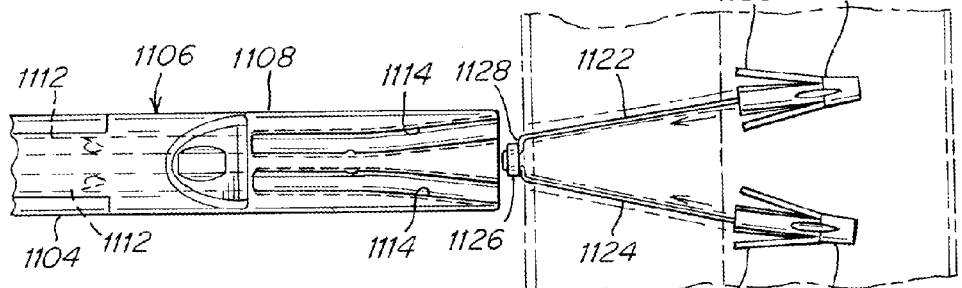

An instrument 1100 for delivering a transfascial suture is shown in FIGS. 33-33B and may include a reusable unit and a disposable unit similar to those described above in connection with the instrument of FIGS. 9-13. The reusable unit 1102 may include a handle (not shown), an elongated shaft 1104 and a drive assembly included within and actuatable at the handle. The disposable unit 1106 may include a tip 1108 and suture assembly 1110. The reusable unit includes a pair of drive elements 1112, which may be in the form of needles, that extend along the elongated shaft and are deployable and retractable in response to actuation of a control mechanism at the handle.

As shown, the path 1114 of the drive elements or needles may diverge, increasing the spacing between the needles beyond the instrument and the amount of tissue purchase thereby. Alternatively, the drive element paths may be parallel or converging.

An implantable suture retainer 1120 may be located in each of the drive paths, with each retainer connected to one of the suture segments 1122, 1124 extending through the opening or openings in the tip body. The suture retainers are adapted to receive and be carried by the drive elements 1112 as they are advanced from the shaft of the reusable unit, through the tip body and along and beyond the distal extension of the tip. In one embodiment, the suture retainers each include an axial through-bore for receiving a portion of a needle tip. The bore and/or needle may be configured so only part of the needle will project through the retainer. For example, and without limitation, the needle may include a necked down narrow tip portion that is extendable through and beyond the retainer bore, and a stepped up larger proximal portion that is engageable with the retainer, for example with an internal or external shoulder of the retainer.

Figure 33C:
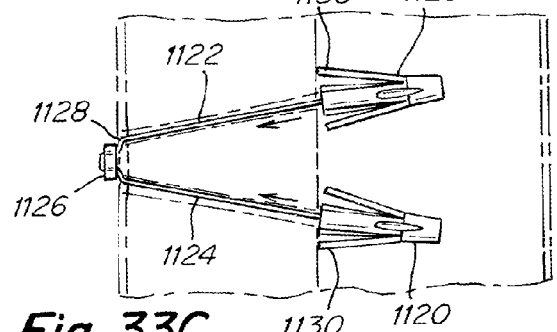

As shown, a force distribution member 1126 may be arranged in floating relationship with the suture segments. As shown in FIG. 33C, after both suture segments are fully deployed out of the instrument, the force distribution member and intermediate segment 1128 will position against the soft tissue repair patch.

The suture retainers 1120 are carried by the needles from the instrument through the soft tissue repair prosthetic and/or fascia, presenting below the skin surface, for example, between the fascia and the skin layer. Upon completion of the instrument stroke, the needles retract back through the fascia and through the abdominal wall patch, leaving a first suture segment 1122 running from a first suture retainer located between the fascia and skin layer, to an intermediate segment 1128 and force distribution member 1126 internal of the abdominal cavity and positionable against the abdominal wall patch, and back to a second segment 1124 running from the force distribution member through the abdominal wall patch and fascia to a second retainer located between the fascia and skin layer.

The retainers may be configured so that they are unlikely to slip back through the needle puncture openings. In one embodiment, the proximal end portion 1130 of a retainer may expand from a collapsed configuration suitable for delivery through the fascia to an expanded configuration after deployment between the fascia and dermal layer. When expanded, the retainers anchor the suture segments in place without tying, or other securing, of the suture tails together. The retainers may be formed of an absorbable material, such as PLA, having sufficient stiffness to anchor the suture and abdominal wall patch in position. However, the retainers may be formed of any suitable material, including non-absorbable material, as should be apparent to one of skill in the art.

The suture may be configured to draw the intermediate segment and/or force distribution member toward the implanted retainers and against the abdominal wall patch. In one embodiment, the suture may be formed of a stretchable material, such as polybutester, that becomes stretched and loaded during deployment of the retainers to thereby tension the suture segments and automatically tighten the suture without having to manually pull the suture or retainers to hoist and/or secure the patch in position. For example, and without limitation, the suture segments may be sized for a deployment of approximately 1.0-1.5 cm through the fascia. During deployment, the suture segments may be over-deployed to approximately 2.0 cm to place sufficient tension on the suture segments for anchoring the patch in position.

An instrument 1200 for delivering a transfascial suture is shown in FIGS. 34-34D and may include a drive element 1202, which may be in the form of a needle, and a suture assembly 1204 supported on the needle. The needle and suture assembly may be housed within an elongated shaft 1206 and may be operated with a drive assembly included within and actuatable at a handle provided at a proximal end of the shaft.

The suture assembly 1204 may include a suture retainer 1208 connected to a first suture segment 1210 and a suture anchor 1212 connected to a second suture segment 1214. As shown, the first suture segment may be slidably received through a locking member 1216, such as a locking knot, provided at the end of the second suture segment and adjacent the suture anchor. A force distribution member 1218 may be arranged in floating relationship with the suture segments.

The suture retainer is adapted to receive and be carried by the needle 1202, or other drive element, as it is advanced from the shaft of the instrument. In one embodiment, the suture retainer includes an axial through-bore for receiving a portion of a needle tip. The bore and/or needle may be configured in a manner similar to arrangements describe above so only part of the needle will project through the retainer. As shown, the suture assembly may extend along the exterior of the needle. However, it is to be appreciated that one or more features of the suture assembly may be carried within the needle. For example, and without limitation, the suture anchor may be received and carried in a corresponding cavity provided on the exterior surface of the needle to position the suture anchor below the skin upon deployment of the suture assembly.

As shown in FIG. 34A, the suture retainer 1208 is carried by the needle from the instrument through the soft tissue repair prosthetic P and/or fascia W, presenting on the other side of the abdominal wall and above the skin surface. Upon completion of the instrument stroke, as shown in FIG. 34B, the needle retracts back through the fascia and the abdominal wall patch, leaving the first suture segment 1210 running from the suture retainer 1208 located exterior of the abdominal cavity, to the force distribution member 1218 internal of the abdominal cavity and positionable against the abdominal wall patch, and back to the second segment 1214 running from the force distribution member through the abdominal wall patch and fascia to the suture anchor 1212 which is located below the skin. The first suture segment 1210 extends through the locking member 1216 adjacent the suture anchor 1212.

As shown in FIG. 34C, the suture assembly may be tightened to draw the force distribution member against the wall patch by holding and pulling the suture retainer to draw a length of the suture segment through the locking member. If desired, a knot pusher 1220 may be slid along the first suture segment external to the abdominal cavity and pushed against the locking member to assist with tightening of the suture assembly. As shown, the suture anchor may be adapted to toggle into an anchoring position as the suture is tightened. When the suture assembly is sufficiently tightened to secure the wall patch, excess length of the first suture segment may be cut below the skin and removed along with the suture retainer.

A method of transfascial suturing, for example in the repair of an abdominal wall defect such as a ventral hernia, will now be described. The patient is prepared in the typical fashion for hernia surgery which may include administration of general anesthesia, identification of the hernia size and location, and shaving, washing and sterilization of the surgical site. The abdominal cavity may be insufflated or otherwise expanded to separate the abdominal wall from organs located in the abdominal cavity. A trocar cannula may be inserted to provide camera access to the cavity allowing the physician to visualize the surgical site. A separate laparoscopic cannula may be inserted into the abdominal wall cavity, or an incision (such as formed by a trocar) may be made leading into the abdominal wall cavity, and an abdominal wall repair prosthetic then may be inserted, as described below, through such cannula, incision, or other passageway into the abdominal cavity.

Figure 35:
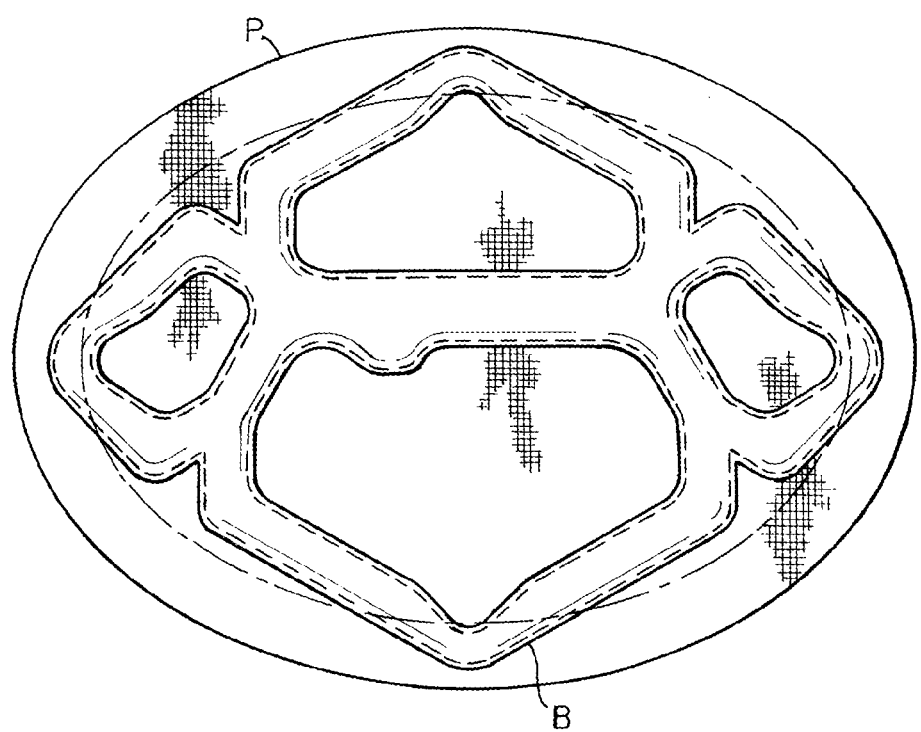
FIG. 35 is an illustration of a ventral repair patch and an inflatable deployment assist device.

The prosthetic, which may be in the form of a patch, preferably is reduced in size to facilitate delivery through the slender cannula or incision. For example, and without limitation, the prosthetic may be rolled, folded, or otherwise collapsed into a shape suitable for passage through the narrow approach to the abdominal cavity. Once located within the cavity, the prosthetic is unfurled or otherwise enlarged, manually or inherently under its own power, and then is positioned relative to the defect, preferably with a margin of at least several centimeters projecting beyond the edges of the defect. Delivery and enlargement of the patch may be facilitated by a mesh introducer such as a PRECISIONPASS instrument available from Davol Inc., assignee of the instant application. Alternatively, a patch deployment assist device, such as an inflatable deployment assist balloon B as illustrated in FIG. 35, may be employed to deliver, expand, and/or position the prosthetic against the abdominal wall relative to the defect.

In a representative method, the patch is reduced along with a deflated deployment assist device, to a slender size such as by rolling the patch and deployment assist device into a cylindrical shape. One or more attachment components on the deployment assist device may help mount the patch to the deployment assist device. An inflation tube for the deployment assist device may be routed through the patch and then grasped, once the deployment assist device and patch are in the abdominal cavity, by a suture passer or other instrument that has been inserted into the abdominal cavity from outside of the patient. The suture passer is withdrawn, externalizing the inflation tube. The end of the inflation tube outside of the patient may be fluidly connected to an inflation source. Introduction of an inflation medium through the inflation tube will expand the balloon, unfurling the patch into a substantially planar configuration or such other end-use configuration as may be desired. The patch is positioned relative to the defect and when appropriately located, the inflation tube may be pulled from outside of the patient to hoist the deployment assist device and, consequently, the patch carried thereby against the abdominal wall. A hemostat, clamp or other instrument, may be applied to the inflation tube to retain the deployment assist device in position. If desired, the patch still may be rotated to optimize angular orientation of the patch.

The prosthetic patch may be maintained in position against the abdominal wall by the deployment assist device or, alternatively, by use of laparoscopic instruments such as graspers. At this time, in the discretion of the physician, a plurality of coils, tacks, staples, or other mechanical fixation elements may be applied through the patch into the abdominal wall.

A single or twin-needle, or other single or twin-drive element, suture delivery instrument is then inserted through the cannula or narrow incision into the abdominal cavity. The instrument includes one or more suture and suture force distribution member assemblies, such as any of the arrangements previously described. From within the abdominal cavity and under camera visualization, the tip of the suture delivery instrument is placed against a margin of the patch, or other location as desired by the physician. At least one trigger or other control is actuated, from outside of the patient, driving one needle or a pair of needles simultaneously or in a sequence, through the distal end of the instrument where the needles associate, if they were not pre-associated, with respective suture segments. The needle or needles advance out of the instrument and pierce through the patch margin, the abdominal wall (fascia) and, if desired, also through subcutaneous tissue, fat and skin, with the needles paying out the suture segments as they travel through the patch and anatomy.

The tail ends or sections of the suture segments may be retained on the exterior side of the abdominal cavity by application of hemostats, clamps, or other devices, or by grasping by medical staff, to prevent the suture segments from slipping back into the abdominal cavity, as well as to maintain tension on the sutures thereby keeping the patch positioned against the internal abdominal wall. The tail ends or sections external of the abdominal cavity may be pulled to hoist the patch against the abdominal wall and then the hemostats or other instruments applied, or reapplied, to manage the suture ends and patch location. In certain embodiments, suture retainers, such as those previously described, may be employed to manage the suture tails post deployment.

As the suture is delivered through the fascia, and/or in response to the pulling, external of the abdominal cavity, of the suture tails or segments that have been delivered through the fascia, a suture force distribution member becomes lodged against the prosthetic inside of the abdominal wall cavity. Advantageously, the puncture openings through the patch formed by the needles are covered, at least in part, by the force distribution member. By covering the puncture openings, the suture force distribution member helps prevent adhesions between the viscera and the tissue infiltratable side of the patch. The delivery of sutures may be repeated, for example at spaced locations about the periphery of the patch, and either after deployment of each suture or after all of the sutures have been delivered, respective suture tail pairs may be knotted, excess suture length trimmed, and the skin over the suture knot closed by stitching, adhesive strip or otherwise. The deployment assist device may be separated from the patch and removed at any time after proper positioning of the patch, and preferably after the patch has at least been provisionally secured such as by initial suturing or mechanical fixation, and may remain in the abdominal cavity until transfascial suturing has been completed. As mentioned, mechanical fixation elements may, at the discretion of the physician, be applied to the patch prior to transfascial suturing. Alternatively, such mechanical fixation may occur after transfascial suturing, or the transfascial suturing procedure may be concluded without deploying any mechanical fixation elements.

The soft tissue repair prosthetic may be formed of a porous material, such as a knit, woven or non-woven fabric, or may be composed of a solid, substantially non-porous, or micro-porous material. The prosthesis may be formed of one or more layers of the same or dissimilar material, and the layers may be stacked one on top of the other, side-to-side, or include a combination of both stacking arrangements. The prosthesis may be formed with portions that are tissue infiltratable and other portions that are less tissue infiltratable or are non-tissue infiltratable, providing selected areas of the repair device with different tissue ingrowth and adhesion resistant properties. The prosthesis may be formed of permanent material, resorbable material, or a combination of permanent and resorbable materials. It should be appreciated that the prosthesis may be formed of any biologically compatible material, synthetic or natural, suitable for repairing a tissue or muscle wall defect as would be apparent to one of skill in the art. Depending upon the surgical application, the prosthesis may be in the form of a patch, plug or combination patch and plug.

In a representative embodiment, the soft tissue repair prosthetic is in the form of a ventral hernia repair patch, and may include a tissue infiltratable layer and a barrier layer. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. In the described method of ventral hernia repair, the polypropylene side would face the abdominal wall and the ePTFE side would face the viscera.

Surgical materials which are suitable for tissue or muscle reinforcement and defect correction may be utilized include, but are not limited to, BARD MESH (available from C.R. Bard, Inc.), SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Biologic materials, including XENMATRIX, COLLAMEND, and ALLOMAX (all available from C.R. Bard, Inc.) or COOK SURGISIS (available from Cook Biomedical, Inc.) may also be used. Resorbable materials, including polyglactin (VICRYL—available from Ethicon, Inc.) and polyglycolic acid (DEXON—available from US Surgical, Inc.). These materials may be used alone in a soft tissue repair prosthetic, in combination with one another, or in combination with other materials. The fabric may be formed from multifilament yarns and any suitable method, such as knitting, weaving, braiding, molding and the like, may be employed to form the mesh material. It should be appreciated that when the soft tissue repair prosthesis is in the form of a patch, it may be configured in many shapes, including, but not limited to substantially flat, concave, convex, and concave-convex, and may, for example, be in the shape of a square, rectangle, circle, or ellipse. Further, the patch may be loaded with one or more drugs including, without limitation, an analgesic or antibiotic.

The suture may be formed of a synthetic or natural material, and may be absorbable or non-absorbable. For some applications, the suture may be formed of a stretchable material. Representative suture materials include, but are not limited to, polypropylene, PTFE, nylon, polyester, polybutester, silk, PGA, PLA/PGA, caprolactone, catgut, polyhydroxyalkanoate and PDO.

The above and other aspects of the invention will be appreciated from the detailed description and claims. It should be understood that although aspects of the invention have been described with reference to illustrative embodiments, aspects of the invention are not limited to the embodiments described. Also, aspects of the invention may be used alone, or in any suitable combination with other aspects of the invention.

What is claimed is:

1. A method of delivering a transfascial suture, the method comprising acts of:
    (a) providing a soft tissue repair prosthetic and a suturing instrument in an abdominal cavity of a patient with the soft tissue repair prosthetic located between the suturing instrument and the abdominal wall, the soft tissue repair prosthetic including a first surface facing away from the abdominal wall and a second surface facing toward the abdominal wall, the suturing instrument including a distal end facing the first surface and the suturing instrument not passing through the soft tissue repair prosthetic, the suturing instrument including a suture defined by a pair of suture segments and an intermediate segment extending continuously between and connecting the suture segments, the intermediate segment including a suture force distributing member;
    (b) passing, from within the abdominal cavity, each suture segment in a distal direction beyond the distal end of the suturing instrument first through the first surface of the soft tissue repair prosthetic and then through the second surface and at least a part of the abdominal wall; and
    (c) positioning the suture force distributing member against the first surface of the soft tissue repair prosthetic to spread forces applied along the intermediate segment.

2. The method of claim 1, wherein act (c) includes preventing passage of the intermediate segment through the soft tissue repair prosthetic.

3. The method of claim 1, wherein act (b) includes simultaneously passing the pair of suture segments from the suturing instrument through the soft tissue repair prosthetic and then through the at least a part of the abdominal wall.

4. The method of claim 1, wherein act (b) includes piercing the soft tissue repair prosthetic and then piercing the at least a part of the abdominal wall.

5. The method of claim 1, further comprising repeating act (b) in one or more locations about a peripheral segment of the soft tissue repair prosthetic.

6. The method of claim 1, wherein the soft tissue repair prosthetic is in the form of a patch.

7. The method of claim 1, further comprising, after act (b), securing the suture segments together outside the abdominal cavity.

8. The method of claim 1, wherein during act (b) the suture force distributing member is not fixedly secured to a position on the suture.

9. The method of claim 1, further comprising, before act (b), non-suture fixating the soft tissue repair prosthetic to the abdominal wall.

10. The method of claim 9, wherein the act of non-suture fixating includes one or more acts of tacking, screw fastening or helicoil fastening the soft tissue repair prosthetic to the abdominal wall.

11. The method of claim 1, further comprising after act (b), non-suture fixating the soft tissue repair prosthetic to the abdominal wall.

12. The method of claim 11, wherein the act of non-suture fixating includes one or more acts of tacking, screw fastening or helicoil fastening the soft tissue repair prosthetic to the abdominal wall.

13. The method of claim 1, wherein act (b) includes an act of passing a pair of suture retainers, each connected to a respective suture segment, from within the abdominal cavity through the soft tissue repair prosthetic and the at least part a of the abdominal wall to outside the abdominal cavity.

14. The method of claim 13, after act (b), further including an act of reorienting the suture retainers.

15. The method of claim 13, after act (b), further including an act of adjusting the relative position of at least one of the suture retainers and the respective suture segment.

16. The method of claim 15, wherein the act of adjusting includes pulling a length of the respective suture segment through the at least one of the suture retainers.

17. The method of claim 15, wherein the act of adjusting includes moving the at least one of suture retainers along a length of the respective suture segment.

18. The method of claim 1, wherein act (b) includes passing the pair of suture segments in substantially parallel paths through the at least a part of the abdominal wall.

19. The method of claim 1, wherein act (b) includes passing the pair of suture segments in diverging paths through the at least a part of the abdominal wall.

20. The method of claim 1, wherein act (b) includes passing the pair of suture segments through fascia and muscle and further through skin.

21. The method of claim 1, further comprising, before act (b), the act of inserting a deployment assist device into the abdominal cavity and positioning, with the deployment assist device, the soft tissue repair prosthetic against the abdominal wall.

22. The method of claim 21, wherein the inserting step includes mounting the soft tissue repair prosthetic to the deployment assist device before inserting the deployment assist device into the abdominal cavity.

23. The method of claim 22, wherein the deployment assist device is inflatable.

24. The method of claim 1, wherein act (b) includes associating at least one of the suture segments with a needle and passing the associated needle with the at least one of the suture segments through the soft tissue repair prosthetic and the at least a part of the abdominal wall.

25. The method of claim 24, wherein a length of the at least on of the suture segments is contained within the associated needle.

26. The method of claim 25, wherein the length of suture segment plays out of the associated needle as the needle is passing through the soft tissue repair prosthetic and at least part of the abdominal wall.

27. The method of claim 1, wherein the pair of suture segments each include a free end section and a proximal section, and act (b) includes passing the free end section, before the proximal section, through the soft tissue repair prosthetic.

28. The method of claim 1, wherein the pair of suture segments each include a free end section and a proximal section, and act (b) includes passing the proximal section before the free end section through the soft tissue repair prosthetic.

29. A method of delivering a transfascial suture, the method comprising acts of:
(a) inserting a suturing instrument into an abdominal cavity, the suturing instrument having a pair of needles and loaded with at least one continuous suture defined by a pair of suture segments, each suture segment connected to a suture retainer, each needle associated with one of the suture retainers, the suturing instrument including a distal end with each needle being extendable beyond the distal end:
(b) advancing each of the needles in a distal direction beyond the distal end of the suturing instrument and in the distal direction outwardly from within the abdominal cavity through at least a part of the abdominal wall, and passing each suture retainer outwardly from within the abdominal cavity through the at least a part of the abdominal wall; and
(c) retracting each of the needles inwardly back through the at least a part of the abdominal wall and into the abdominal cavity to deploy each suture retainer outside the abdominal cavity by separating each suture retainer from the suturing instrument while the suturing instrument is located within the abdominal cavity.

30. The method of claim 29, wherein act (b) includes advancing each of the needles through a soft tissue repair prosthetic before advancing each of the needles through the at least a part of the abdominal wall.

31. The method of claim 30, wherein act (b) includes simultaneously passing the pair of needles through the soft tissue repair prosthetic and the at least a part of the abdominal wall.

32. The method of claim 30, further comprising repeating act (b) in one or more locations about a peripheral segment of the soft tissue repair prosthetic.

33. The method of claim 30, wherein the suture includes a suture force distributing member and act (b) includes positioning the suture force distributing member against the soft tissue repair prosthetic.

34. The method of claim 33, wherein during act (b) the suture force distributing member is not fixedly secured to a position on the suture.

35. The method of claim 30, further comprising, before act (b), non-suture fixating the soft tissue repair prosthetic to the abdominal wall.

36. The method of claim 35, wherein the act of non-suture fixating includes one or more acts of tacking, screw fastening or helicoil fastening the soft tissue repair prosthetic to the abdominal wall.

37. The method of claim 30, further comprising after act (b), non-suture fixating the soft tissue repair prosthetic to the abdominal wall.

38. The method of claim 37, wherein the act of non-suture fixating includes one or more acts of tacking, screw fastening or helicoil fastening the soft tissue repair prosthetic to the abdominal wall.

39. The method of claim 30, further comprising, before act (b), the act of inserting a deployment assist device into the abdominal cavity and positioning, with the deployment assist device, the soft tissue repair prosthetic against the abdominal wall.

40. The method of claim 39, wherein the deployment assist device is inflatable.

41. The method of claim 29, wherein the suture includes an intermediate segment between the pair of suture segments, and wherein act (b) includes not passing the intermediate segment through any part of the abdominal wall.

42. The method of claim 29, further comprising, after act (b), securing the pair of suture segments together outside the abdominal cavity.

43. The method of claim 29, after act (b), further including an act of reorienting the suture retainers.

44. The method of claim 43, after act (b), further including an act of adjusting the relative position of at least one of the suture retainers and an associated suture segment.

45. The method of claim 44, wherein the act of adjusting includes pulling a length of the associated suture segment through the at least one of the suture retainers.

46. The method of claim 44, wherein the act of adjusting includes moving the at least one of suture retainers along a length of the associated suture segment.

47. The method of claim 29, wherein act (b) includes advancing the pair of needles in substantially parallel paths through the at least a part of the abdominal wall.

48. The method of claim 29, wherein act (b) includes advancing the pair of needles in diverging paths through the at least a part of the abdominal wall.

49. The method of claim 29, wherein act (b) includes passing the pair of suture segments through fascia and muscle and further through skin.

50. The method of claim 29, wherein the pair of suture segments each include a tail section and a proximal section, and act (b) includes passing the tail section, before the proximal section, through the at least part of the abdominal wall.

51. A method of delivering a transfascial suture, the method comprising acts of:
  (a) providing a soft tissue repair prosthetic in an abdominal cavity, the soft tissue repair prosthetic including a first surface facing away from the abdominal wall and a second surface facing toward the abdominal wall;
  (b) providing a suturing instrument including a distal end in the abdominal cavity with the distal end of the suturing instrument facing the first surface and the suturing instrument not passing through the soft tissue repair prosthetic, the suturing instrument including a suture defined by a pair of suture segments and an intermediate segment extending continuously between and connecting the pair of suture segments, each suture segment including a suture retainer;
  (c) passing, from within the abdominal cavity, each of the suture retainers in a distal direction beyond the distal end of the suturing instrument first through the first surface of the soft tissue repair prosthetic and then through the second surface of the soft tissue repair prosthetic and at least a part of the abdominal wall to outside the abdominal cavity, each of the suture segments following a respective suture retainer through the soft tissue repair prosthetic and abdominal wall; and
  (d) after act (c), securing together the pair of suture segments outside the abdominal cavity.

52. The method of claim 51, wherein act (c) includes not passing the intermediate segment through the soft tissue repair prosthetic.

53. The method of claim 51, wherein act (c) includes piercing the soft tissue repair prosthetic and then piercing the at least a part of the abdominal wall.

54. The method of claim 51, wherein act (c) includes simultaneously passing the pair of suture retainers through the soft tissue repair prosthetic and then through the at least a part of the abdominal wall.

55. The method of claim 51, further comprising repeating acts (b)-(c) in one or more locations about a peripheral segment of the soft tissue repair prosthetic.

56. The method of claim 51, wherein the soft tissue repair prosthetic is in the form of a patch.

57. The method of claim 51, wherein the suture includes a force distributing member and act (c) includes positioning the force distributing member against the soft tissue repair prosthetic.

58. The method of claim 57, wherein during act (c) the force distributing member is not fixedly secured to a position on the suture.

59. The method of claim 51, further comprising, before act (c), non-suture fixating the soft tissue repair prosthetic to the abdominal wall.

60. The method of claim 59, wherein the act of non-suture fixating includes one or more acts of tacking, screw fastening or helicoil fastening the soft tissue repair prosthetic to the abdominal wall.

61. The method of claim 51, further comprising after act (c), non-suture fixating the soft tissue repair prosthetic to the abdominal wall.

62. The method of claim 61, wherein the act of non-suture fixating includes one or more acts of tacking, screw fastening or helicoil fastening the soft tissue repair prosthetic to the abdominal wall.

63. The method of claim 51, after act (c), further including an act of reorienting the suture retainers.

64. The method of claim 51, after act (c), further including an act of adjusting the relative position of at least one of the suture retainers and an associated suture segment.

65. The method of claim 64, wherein the act of adjusting includes pulling a length of the associated suture segment through the at least one of the suture retainers.

66. The method of claim 64, wherein the act of adjusting includes moving the at least one of the suture retainers along a length of the associated suture segment.

67. The method of claim 51, wherein act (c) includes passing the pair of suture retainers in substantially parallel paths through the at least a part of the abdominal wall.

68. The method of claim 51, wherein act (c) includes passing the pair of suture retainers in diverging paths through the at least a part of the abdominal wall.

69. The method of claim 51, wherein act (c) includes passing the pair of suture retainers through fascia and muscle and further through skin.

70. The method of claim 51, further comprising, before act (c), the act of inserting a deployment assist device into the abdominal cavity and positioning, with the deployment assist device, the soft tissue repair prosthetic against the abdominal wall.

71. The method of claim 70, wherein the deployment assist device is inflatable.

72. The method of claim 51, wherein the soft tissue repair prosthetic is located between the suturing instrument and the abdominal wall.

73. A method of delivering a transfascial suture, comprising acts of:
(a) providing a soft tissue repair prosthetic and a suturing instrument loaded with a suture and a force distributing member in an abdominal cavity, the soft tissue repair prosthetic including a first surface facing away from the abdominal wall and a second surface facing toward the abdominal wall, the suturing instrument including a distal end in the abdominal cavity with the distal end of the suturing instrument facing the first surface and the suturing instrument not passing through the soft tissue repair prosthetic;
(b) after act (a), creating an opening through the soft tissue repair prosthetic using an inside-out technique by first passing, from within the abdominal cavity, the suture through the first surface of the soft tissue repair prosthetic and then through the second surface before passing the suture through at least a part of the abdominal wall; and
(c) covering, from within the abdominal cavity, at least part of the opening in the soft tissue repair prosthetic with the force distributing member carried by the suture.

74. The method recited in claim 73, wherein act (b) includes puncturing, within the abdominal cavity, the opening in the soft tissue repair prosthetic.

75. The method recited in claim 74, wherein the puncturing act within the abdominal cavity includes advancing a needle associated with the suture through the soft tissue repair prosthetic.

76. The method recited in claim 73, wherein the force distributing member has a tubular configuration or a substantially planar configuration.

77. The method recited in claim 73, where the force distributing member is not fixedly secured to a position on the suture.

78. The method recited in claim 73, wherein the force distributing member includes a surface feature adapt to engage with the soft tissue repair prosthetic.

79. The method recited in claim 73, wherein the suturing instrument includes a pair of needles for delivering segments of the suture through the soft tissue repair prosthetic.

* * * * *

UNITED STATES PATENT AND TRADEMARK OFFICE
CERTIFICATE OF CORRECTION

| | | |
|---|---|---|
| PATENT NO. | : 9,439,643 B2 | Page 1 of 1 |
| APPLICATION NO. | : 13/157155 | |
| DATED | : September 13, 2016 | |
| INVENTOR(S) | : Roger E. Darois et al. | |

It is certified that error appears in the above-identified patent and that said Letters Patent is hereby corrected as shown below:

In the Claims

At Column 23, Claim 17, Line 37, replace "of suture retainers" with —of the suture retainers—

At Column 23, Claim 25, Line 66, replace "least on" with —least one—

At Column 24, Claim 29, Line 25, replace "beyond the distal end:" with —beyond the distal end;—

At Column 25, Claim 46, Line 28, replace "one of suture retainers" with —one of the suture retainers—

Signed and Sealed this
Third Day of January, 2017

Michelle K. Lee
*Director of the United States Patent and Trademark Office*